United States Patent [19]
Bender et al.

[11] Patent Number: 5,134,150
[45] Date of Patent: Jul. 28, 1992

[54] INHIBITION OF THE 5-LIPOXYGENASE PATHWAY

[75] Inventors: Paul E. Bender, Cherry Hill; John G. Gleason, Delran, both of N.J.; Don E. Griswold, North Wales, Pa.; Nabil Hanna, Berwyn, Pa.; Ivan Lantos, Blackwood, N.J.; Kazys A. Razgaitis, Rosemont, Pa.; Henry M. Sarau, Hatfield, Pa.; Susan C. Shilcrat, Bala Cynwyd, Pa.

[73] Assignee: SmithKline Beecham Corporation, Philadelphia, Pa.

[21] Appl. No.: 445,581

[22] Filed: Dec. 4, 1989

Related U.S. Application Data

[63] Continuation of Ser. No. 106,199, Oct. 7, 1987, abandoned, which is a continuation-in-part of Ser. No. 856,875, Apr. 28, 1986, abandoned, which is a continuation-in-part of Ser. No. 808,595, Dec. 12, 1985, abandoned.

[51] Int. Cl.$^5$ .............. A61K 31/44; A61K 31/445; A61K 31/415; A61K 31/425
[52] U.S. Cl. .............. 514/318; 514/322; 514/333; 514/338; 514/368; 514/187; 546/199; 546/256; 546/271; 548/154
[58] Field of Search .............. 548/154; 546/199, 187, 546/256, 271; 514/368, 318, 322, 333, 338

[56] References Cited

U.S. PATENT DOCUMENTS

| | | | |
|---|---|---|---|
| 3,823,239 | 7/1974 | Fox et al. | 546/256 |
| 4,064,260 | 12/1977 | Cherkofsky et al. | 546/256 |
| 4,110,460 | 8/1978 | Baetz et al. | 546/256 |
| 4,153,706 | 5/1979 | Bender et al. | 546/256 |
| 4,175,127 | 11/1979 | Bender et al. | 546/256 |
| 4,186,205 | 1/1980 | Bender et al. | 546/256 |
| 4,263,311 | 4/1981 | Bender et al. | 546/256 |
| 4,507,481 | 3/1985 | Davidson et al. | 546/256 |

FOREIGN PATENT DOCUMENTS

| | | |
|---|---|---|
| 154494 | 9/1985 | European Pat. Off. |
| 1180202 | 2/1970 | United Kingdom |
| 2039882 | 8/1980 | United Kingdom |

OTHER PUBLICATIONS

Lantos et al., *J. Med. Chem.*, 27, 72–75 (1984).
Bender et al., *J. Med. Chem.*, 28, 1169–1177 (1985).
Claxton, G. P., *J. Med. Chem.*, 17, 3, 364–367 (1974).
Kano, S., *J. Pharm. Soc. Japan*, 92, 1, 55–58 (1972).
Andreani, A. et al., *Arch. Pharm.* (Weinheim), 315, 451–456 (1982).
Schoberl, A. et al., *Liebigs Ann. Chem.*, 742, 85–97 (1970).
Lee, M. H., *Biochemical Pharmacology*, 24, 1175–1178 (1975).
Andreani, A. et al., *Eur. J. Med. Chem.*, 19, 3, 219–222 (1984).
Koyama, K. et al., *Oyo Yakura Pharmacometrics*, 26, 6, 869–876 (1983).
*Chem. Abs.* 111994 q, vol. 82, p. 507 (1975).
Mohrle, H., *Arch. Pharm.* (Weinheim), 316, 47–55 (1983).

*Primary Examiner*—Johann Richter
*Attorney, Agent, or Firm*—Dara L. Dinner; Stuart R. Suter; Edward T. Lentz

[57] ABSTRACT

A method of inhibiting the 5-lipoxygenase pathway in an animal in need thereof which comprises administering an effective, 5-lipoxygenase pathway inhibiting amount of a diaryl- substituted imidazole fused to a thiazole pyrrolidine, thiazide or piperidine ring to such animal.

42 Claims, No Drawings

INHIBITION OF THE 5-LIPOXYGENASE PATHWAY

CROSS-REFERENCE TO RELATED APPLICATION

This is a continuation of application Ser. No. 106,199 filed on Oct. 7, 1987, now abandoned, which is a continuation-in-part of application Ser. No. 856,875 filed on Apr. 28, 1986, now abandoned, which is a continuation-in-part of application Ser. No. 808,595, filed Dec. 12, 1985, now abandoned.

BACKGROUND OF THE INVENTION

This invention relates to novel compounds, pharmaceutical compositions and a method of inhibiting the 5-lipoxygenase pathway of arachidonic acid metabolism in an animal in need thereof which comprises administering to such animal an effective, 5-lipoxygenase pathway inhibiting amount of a diaryl-substituted imidazole fused to a thiazole, pyrrolidine, thiazine or piperidine ring or a pharmaceutically acceptable salt thereof.

Ciba-Geigy AG., U.K. Patent Application GB 2,039,882, published Aug. 20, 1980, discloses compounds of the formula

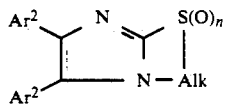

wherein the 1,3-diazacyclopent-2-ene ring may have a further double bond, Alk represents lower alkylene that separates the sulfur atom from the nitrogen atom by 2 to 4 carbon atoms, $Ar_1$ and $Ar_2$ represent, independently of one another, an optionally substituted phenyl, pyridyl or thienyl radical and n is 0, 1 or 2, provided that at least one of the radicals $Ar_1$ and $Ar_2$ is not phenyl when Alk represents ethylene and the 1,3-diazacyclopent-2-ene ring represents an imidazole ring, and the salts thereof. Compound 1 is not specifically disclosed. The Ciba-Geigy reference alleges that such compounds exhibit anti-inflammatory and antiexudation effects in the rat kaolin paw-oedema test or in the rat turpentine pleuritis test; that the unsaturated compounds in particular exhibit an excellent effect in the adjuvant arthritis test; and that such compounds also have an analgesic effect as shown in the phenyl-p-benzoquinone test in mice; inhibit prostaglandin synthetase in vitro; protect against fatal pulmonary embolism in rabbits (i.e., are anti-thrombotic); and that the tetrahydro compounds exhibit a strong effect in the pertussis oedema test. The rat kaolin paw oedema test and the rat turpentine pleuritis test are useful in detecting compounds which are cyclooxygenase inhibitors but are of no known utility in detecting or suggesting compounds which are inhibitors of the 5-lipoxygenase pathway. The adjuvant arthritis test is useful for detecting compounds which are inhibitors of prostanoid synthesis, but is of no utility for disclosing or suggesting compounds which are inhibitors of the 5-lipoxygenase pathway. The phenyl-p-benzoquinone test is useful for detecting compounds which are cyclooxygenase inhibitors, but is of no known utility in detecting or suggesting compounds which are inhibitors of the 5-lipoxygenase pathway. The observation that compounds of the Ciba-Geigy reference inhibit prostaglandin synthetase in vitro (cyclooxygenase) is of no utility in detecting or suggesting compounds which are inhibitors of the 5-lipoxygenase pathway. The observation that the compounds of the Ciba-Geigy reference are anti-thrombotic in rabbits is of no known utility in detecting or suggesting compounds which are inhibitors of the 5-lipoxygenase pathway. The pertussis oedema test is useful in detecting compounds which are cyclooxygenase inhibitors, but is of no known utility in detecting or suggesting compounds which are inhibitors of the 5-lipoxygenase pathway.

Bender et al., U.S. Pat. No. 4,175,127, issued Nov. 20, 1979 disclose compounds of the formula

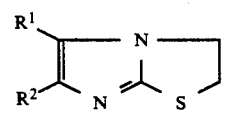

in which $R_1$ and $R_2$ are the same or different, but one of which always being pyridyl, are pyridyl or phenyl optionally monosubstituted by a lower alkoxy, lower alkyl, lower alkylthio, chloro, fluoro, bromo, or trifluoromethyl or a pharmaceutically acceptable acid addition salt or oxide derivative thereof. Bender et al. also discloses that such compounds have utility as antiarthritic agents. Such antiarthritic activity is disclosed as the result of test results from adjuvant-induced polyarthritis in rats. Although not claimed, the Bender patent also suggests, at column 3, lines 66–68, that compounds of Formula A also have antiinflammatory or immunoregulatory properties in addition to their antiarthritic activity. The Bender patent states, at column 4, lines 47–50, that such anti-inflammatory activity is produced by some of the Formula A compounds in the carrageenan-induced rat paw edema test. The Bender patent also states, at column 4, lines 51–65, that species of the Formula A compounds have the ability to regulate cell-mediated immunity as shown in procedures such as the oxazolone-induced contact sensitivity test procedure in which mouse paw volume is measured.

Lantos et al., *J. Med. Chem.*, 27, 72–75 (1984), also disclose that certain 5,6-diaryl-2,3-dihydroimidazo [2,1-b]thiazoles have antiinflammatory activity in the carrageenan-induced rat paw edema and adjuvant arthritis assay in rats. Both the adjuvant-induced polyarthritis assay in rats and the carrageenan-induced rat paw edema test are useful in detecting compounds which are inhibitors of prostanoid synthesis, mediated by the prostanoids formed by the enzyme cyclooxygenase, but are of no known utility in detecting or suggesting compounds which are inhibitors of the generation of 5-lipoxygenase products (such as HETES, LTB4 and peptidoleukotrienes). The oxazolone-induced contact sensitivity test in which mouse paw volume is measured is useful in detecting compounds which are immunostimulatory, but is of no known utility in detecting or suggesting compounds which are inhibitors of the 5-lipoxygenase pathway.

Lantos et al., U.S. Ser. No. 737,137, filed May 29, 1985, disclose an improved method for the preparation of compounds of the formula:

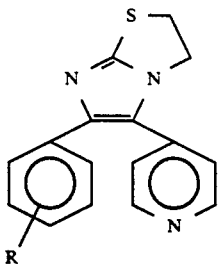

in which R is H, halo, $C_{1-2}$-alkyl, $C_{1-2}$-alkoxy or trifluoromethyl. Lantos et al. state that such compounds have antiarthritic activity. There is no further statement in this reference as to how such antiarthritic activity was determined. Such a blanket statement of anti-arthritic utility does not disclose to one of skill in the art that such compounds have 5-lipoxygenase pathway inhibiting activity. Lantos et al. also disclose compounds of the formula:

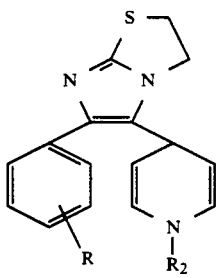

in which:
R is H, halo, $C_{1-2}$ alkyl, $C_{1-2}$ alkoxy or trifluoromethyl;
$R^2$ is H or

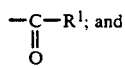

R is $C_{1-8}$ alkyl, $C_{1-8}$ alkoxy, phenyl, phenoxy, benzyl or benzyloxy.

Cherkofsky et al., U.S. Pat. No. 4,064,260, issued Dec. 20, 1977 discloses compounds of the formula

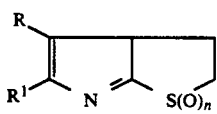

in which n is 0, 1 or 2, and R and $R^1$ are independently selected from monosubstituted phenyl wherein said substituent is selected from $C_{1-4}$ alkoxy. Cherkofsky et al. also disclose that such compounds have utility as antiinflammatory agents as demonstrated by their activity in the established adjuvant-induced arthritis assay in rats or the phenylquinone writhing test in mice. As stated above, the adjuvant arthritis test is of no utility for disclosing or suggesting compounds which are inhibitors of the 5-lipoxygenase pathway. The phenylquinone writhing test is useful for detecting compounds which are inhibitors of prostanoid synthesis but is of no known utility for disclosing or suggesting compounds which are inhibitors of the 5-lipoxygenase pathway.

Bender et al., U.S. Pat. No. 4,263,311 issued Apr. 21, 1981, discloses compounds of the formula

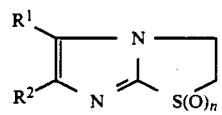

wherein n is 0, 1 or 2, and $R^1$ and $R^2$ are independently selected from (a) monosubstituted phenyl wherein said substituent is selected from lower alkoxy, chloro, fluoro, bromo, trifluoromethyl, amino, di-N-N-lower alkylamino or (b) 3,4-methylenedioxyphenyl. Bender et al. also disclose that such compounds have utility (a) in the treatment of arthritis based on their activity in the adjuvant-induced arthritis test in rats and in the carrageenan-induced rat paw edema test; and (b) as immunoregulatory agents based on their activity in the oxazolone-induced contact sensitivity test in which mouse paw volume is measured. As stated above, none of the adjuvant arthritis test, carrageenan edema test or oxazalone sensitivity test have any known utility in detecting or suggesting compounds which are inhibitors of the 5-lipoxygenase pathway.

Bender et al., U.S. Pat. No. 4,186,205, issued Jan. 29, 1980, disclose compounds of the formula

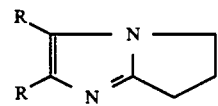

wherein R is 4-monosubstituted phenyl and said substituent is selected from $C_{1-4}$ alkoxy or chloro, or a nontoxic, pharmaceutically acceptable salt thereof. Bender et al. also disclose that such compounds are useful as (a) antiarthritic agents based on their activity in the adjuvant-induced arthritis assay in rats; and (b) regulators of cell-mediated immunity based on their activity in the oxazolone-induced contact sensitivity test in which mouse paw volume is measured. As stated above, neither the adjuvant arthritis test nor the oxazolone sensitivity test are of any known utility in disclosing or suggesting compounds which are inhibitors of the 5-lipoxygenase pathway.

Bender et al., J. Med. Chem., 28, 1169-1177 (1985), disclose compounds of the formula

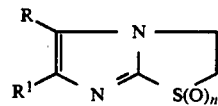

wherein n is 0, 1 or 2, and R and $R^1$ are independently selected from (a) monosubstituted phenyl wherein said substituent is selected from $C_{1-4}$ alkoxy, halo, 4-amino, 4-acetamido, 4-trifluoromethyl, 4-N(ethyl)-acetamido, 4-ethylamino, and 4-ethyl(methyl)amino; or (b) 3,4-methylenedioxyphenyl. Bender et al. also disclose that some of such compounds are useful as immunoregulatory, anti-inflammatory and antiarthritic agents based on their activity in the adjuvant-induced arthritis test and the mouse subliminal oxazolone-induced contact sensitivity assay. As stated above, the adjuvant arthritis assay is of no utility in detecting or suggesting compounds which are inhibitors of the 5-lipoxygenase pathway. The mouse subliminal oxazolone sensitivity assay is useful in detecting compounds which are immunostimulatory but is of no known utility in detecting compounds which are inhibitors of the 5-lipoxygenase pathway.

Baetz et al., U.S. Pat. No. 4,110,460, issued Aug. 29, 1978, discloses compounds of the formula

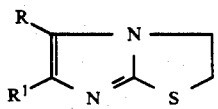

wherein R and R[1] are independently selected from monosubstituted phenyl wherein said substituent is selected from chloro, bromo, C$_{1-4}$ alkoxy, or a pharmaceutically acceptable acid addition salt thereof. Baetz et al. also disclose that such compounds have anti-inflammatory activity based on their activity in the carrageenan-induced edema assay in rats, cotton-induced granuloma assay in rats, ultraviolet induced erythema assay in guinea pigs, and Freund-adjuvant induced arthritis assay in rats. All of such assays are useful for detecting compounds which are inhibitors of prostanoid synthesis, but none of such assays is of any known utility for disclosing or suggesting compounds which are inhibitors of the 5-lipoxygenase pathway. Baetz et al. also disclose that such compounds have utility as antipyretic agents based on their activity in an assay in which hyperthermia was induced in rats by subcutaneous infection with yeast. Such assay is useful for detecting compounds which are cyclooxygenase inhibitors but is of no known utility in detecting or suggesting compounds which are inhibitors of the 5-lipoxygenase pathway. Baetz et al. also disclose that such compounds have analgesic activity based on their activity in the acetic acid writhing test in mice. The acetic acid writhing test is useful for detecting compounds which are cyclooxygenase inhibitors but is of no known utility in detecting compounds which are inhibitors of the 5-lipoxygenase pathway.

Bender et al., U.S. Pat. No. 4,153,706, issued May 8, 1979, disclose compounds of the formula

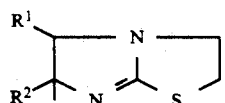

wherein R[1] is 4-substituted phenyl wherein said substituent is selected from lower alkoxy, lower alkylthio, fluoro, chloro, bromo or trifluoromethyl; and R[2] is 4-substituted phenyl wherein said substituent is an election withdrawing group, in particular, fluoro, chloro, bromo or trifluoromethyl. Bender et al. also state that such compounds have antiarthritic activity as measured in the adjuvant-induced polyarthritis assay in rats; and immunoregulatory activity as measured by the oxazolone-induced contact sensitivity test in mice. As stated above, such assays do not disclose or suggest that such compounds have 5-lipoxygenase pathway inhibiting activity.

Davidson et al., U.S. Pat. No. 4,507,481, issued Mar. 26, 1985, disclose compounds of the formula

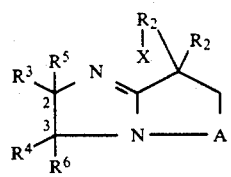

wherein
X is O or S(O)n;
n is 0, 1 or 2;
R$_1$ can be H;
R$_2$ can be H;
A is CH$_2$ or CH$_2$CH$_3$;
R$_3$ and R$_4$ are independently selected from phenyl substituted with lower alkyl, lower alkylamino, lower alkoxy or halogen;
R$_5$ and R$_6$ are each H or join to form a double bond at the 2,3-position.

Davidson et al. also disclose that such compounds are immunostimulants or immunosuppresants based on (a) their inhibiting or stimulating activity in a chemotaxis assay which measures the ability of a drug substance to influence the movement of murine macrophages responding to complement; (b) their immunosuppressing or activating activity in the Kennedy plaque assay in which an animal's humoral immune system is depressed artificially with 6-mercaptopyrine. Such chemotaxis assay is no known utility for detecting or suggesting compounds which are inhibitors of the 5-lipoxygenase pathway. Such Kennedy plaque assay is of no known utility for detecting or suggesting compounds which are inhibitors of the 5-lipoxygenase pathway. Davidson et al. also disclose that such compounds have antiinflammatory activity as determined by the carrageenan-induced paw edema assay in rats. As stated above, such assay has no known utility in detecting or suggesting compounds which are inhibitors of the 5-lipoxygenase pathway. Davidson et al. also disclose that such compounds have antiviral activity in mice with hepatitis; but such activity is of no known utility in detecting or suggesting compounds which are inhibitors of the 5-lipoxygenase pathway.

SUMMARY OF THE INVENTION

This invention relates to a compound of the formula

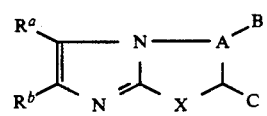

Formula (IB)

wherein:
X is CH$_2$ or S(O)$_n$;
n is 0, 1 or 2;
A is CH$_2$ or CH$_2$CH$_2$;
B and C are independently selected from H, methyl, ethyl or dimethyl;
One of R$^a$ or R$^b$ must be selected from 2-pyridyl, 3-pyridyl, 4-pyridyl, monosubstituted phenyl wherein said substituent is selected from C$_{1-3}$ dialkylamino, C$_{1-3}$ alkylamino, N-(azacyclo C$_{5-6}$ alkyl), cyano, 2,2,2-trihaloethoxy, N-C$_{1-3}$ alkanamido, N-(C$_{1-3}$ alkyl)-(C$_{1-3}$ alkanamido) or prop-2-ene-1-oxy; or disubstituted phenyl wherein said substituents are independently selected from $C_{1-4}$ alkyl or $C_{1-3}$ alkoxy or the disubstituents together form a methylenedioxy group; and the other of $R^a$ or $R^b$ is selected from:
1) pyridyl;
2) phenyl;
3) monosubstituted phenyl wherein said substituent is selected from $C_{1-3}$ alkoxy, halo, $CF_3$, $C_{1-3}$ alkylthio, $C_{1-4}$ alkyl, 2,2,2-trihaloethoxy, prop-2-ene-1-oxy, $C_{1-3}$ alkylamino, $C_{1-3}$ dialkylamino, cyano or N-(azacyclo $C_{5-6}$ alkyl);
4) disubstituted phenyl wherein said substituents are independently selected from $C_{1-4}$ alkyl or $C_{1-3}$ alkoxy or the disubstituents together form a methylene dioxy group; or
5) 3,4,5-trimethoxyphenyl;
provided that:
(a) when X is $CH_2$, both of $R^a$ and $R^b$ are other than pyridyl;
(b) when X is $CH_2$ or S, both of $R^a$ and $R^b$ are other than phenyl substituted in the 2,3,5 or 6 position with $C_{1-3}$ alkylamino; $C_{1-3}$ dialkylamino; or N-(azacyclo $C_{5-6}$ alkyl);
(c) when X is $S(O)_n$ only one of $R^a$ or $R^b$ is $C_{1-3}$ alkylaminophenyl;
(d) when X is $S(O)_n$ only one of $R^a$ or $R^b$ is $C_{1-3}$ dialkylaminophenyl;
(e) when either of $R^a$ or $R^b$ is disubstituted phenyl the other must be 4-pyridyl;
(f) when either of $R^a$ or $R^b$ is cyanophenyl the other must be cyanophenyl or 4-pyridyl;
(g) when X is $S(O)_n$ and either of $R^a$ or $R^b$ is phenyl substituted in the 2,3,5 or 6 position with $C_{1-3}$ alkylamino, $C_{1-3}$ dialkylamino or N-(azacyclo $C_{5-6}$ alkyl), the other must be 4-pyridyl;
(h) when X is $S(O)_n$ only one of $R^a$ or $R^b$ is 4-(prop-2-ene-1-oxy)phenyl;
(i) when X is $S(O)_n$ only one of $R^a$ or $R^b$ is 4-(2,2,2-trifluoroethoxy)phenyl;
(j) when X is $S(O)_n$ only one of $R^a$ or $R^b$ is 3,4-methylenedioxyphenyl;
or a pharmaceutically acceptable salt thereof.

The term "N-(azacyclo $C_{5-6}$ alkyl)" is used herein at all occurrences to mean pyrrolidino or piperidino.

This invention also relates to a pharmaceutical composition comprising a pharmaceutically acceptable carrier or diluent and an effective, non-toxic 5-lipoxygenase pathway inhibiting amount of a compound of

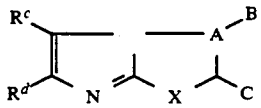

Formula (IC)

wherein:
X is $CH_2$ or $S(O)_n$;
n is 0, 1 or 2;
A is $CH_2$ or $CH_2CH_2$;
B and C are independently selected from H, methyl, ethyl or dimethyl;
One of $R^c$ or $R^d$ must be selected from 2-pyridyl, 3-pyridyl, 4-pyridyl, monosubstituted phenyl wherein said substituent is selected from $C_{1-3}$ dialkylamino, $C_{1-3}$ alkylamino, N-(azacyclo $C_{5-6}$ alkyl), cyano, 2,2,2-trihaloethoxy, N-$C_{1-3}$ alkanamido, N-($C_{1-3}$ alkyl)-($C_{1-3}$ alkanamido) or prop-2-ene-1-oxy; or disubstituted phenyl wherein said substituents are independently selected from $C_{1-4}$ alkyl or $C_{1-3}$ alkoxy or the disubstituents together form a methylenedioxy group; and the other of $R^c$ or $R^d$ is selected from:
1) pyridyl;
2) phenyl;
3) monosubstituted phenyl wherein said substituent is selected from $C_{1-3}$ alkoxy, halo, $CF_3$, $C_{1-3}$ alkylthio, $C_{1-4}$ alkyl, 2,2,2-trihaloethoxy, prop-2-ene-1-oxy, $C_{1-3}$ alkylamino, $C_{1-3}$ dialkylamino, cyano or N-(azacyclo $C_{5-6}$ alkyl);
4) disubstituted phenyl wherein said substituents are independently selected from $C_{1-4}$ alkyl or $C_{1-3}$ alkoxy or the disubstituents together form a methylene dioxy group; or
5) 3,4,5-trimethoxyphenyl;
provided that:
(a) when X is $CH_2$, both of $R^c$ and $R^d$ are other than pyridyl and when X is; $S(O)_n$ and n is 0, both of $R^c$ and $R^d$ are not simultaneously 2-, 3-, or 4-pyridyl; when n is 1, and one of $R^c$ or $R^d$ is 2-pyridyl or 3-pyridyl the other of $R^c$ or $R^d$ is not 2-pyridyl or 3-pyridyl; when n is 2, and one of $R^c$ and $R^d$ is 2-pyridyl the other of $R^c$ and $R^d$ is not 2-pyridyl; and when n is 0 and one of $R^c$ and $R^d$ is phenyl the other of $R^c$ and $R^d$ is not 2-, 3-, or 4-pyridyl;
(b) when X is $CH_2$ or S, both of $R^c$ and $R^d$ are other than phenyl substituted in the 2,3,5 or 6 position with $C_{1-3}$ alkylamino; $C_{1-3}$ dialkylamino; or N-(azacyclo $C_{5-6}$ alkyl);
(c) when X is $S(O)_n$ only one of $R^c$ or $R^d$ is $C_{1-3}$ alkylaminophenyl;
(d) when X is $S(O)_n$ only one of $R^c$ or $R^d$ is $C_{1-3}$ dialkylaminophenyl;
(e) when either of $R^c$ or $R^d$ is disubstituted phenyl the other must be 4-pyridyl;
(f) when either of $R^c$ or $R^d$ is cyanophenyl the other must be cyanophenyl or 4-pyridyl;
(g) when X is $S(O)_n$ and either of $R^c$ or $R^d$ is phenyl substituted in the 2,3,5 or 6 position with $C_{1-3}$ alkylamino; $C_{1-3}$ dialkylamino or N-(azacyclo $C_{5-6}$ alkyl), the other must be 4-pyridyl;
(h) when X is $S(O)_n$ only one of $R^c$ or $R^d$ is 4-(prop-2-ene-1-oxy)phenyl;
(i) when X is $S(O)_n$ only one of $R^c$ or $R^d$ is 4-(2,2,2-trifluoroethoxy)phenyl;
(j) when X is $S(O)_n$ only one of $R^c$ or $R^d$ is 3,4-methylenedioxyphenyl;
(k) when X is $S(O)_n$, and n is 0, and one of $R^c$ or 4-pyridyl, the other is not 4-pyridyl, phenyl, 4-methoxyphenyl, 4-fluorophenyl, 4-methylthiophenyl, 2-bromophenyl, 3-chlorophenyl, 4-trifluoromethylphenyl, 4-methylphenyl, 4-ethylphenyl, [or] 3-isopropoxyphenyl, 4-methoxyphenyl or 4-ethoxyphenyl; and
(l) when $R^d$ is N-($C_{1-3}$ alkanamido) or N-($C_{1-3}$ alkyl)-N-($C_{1-3}$ alkanamido), $R^c$ must be 4-pyridyl;
(m) when X is $S(O)_n$, and n is 1, and one of $R^c$ or $R^d$ is 4-pyridyl, the other is not 4-pyridyl, phenyl, or phenyl mono-substituted by 4-methoxy, 4-ethoxy, or 4-fluoro;
(n) when X is $S(O)n$, and n is 0, 1 or 2, and one of $R^a$ or $R^b$ is phenyl, the other is not a phenyl di-substituted with methoxy;

or a pharmaceutically acceptable salt thereof.

This invention also relates to a method of treating rheumatoid arthritis in an animal in need thereof which comprises administering to such animal an effective, non-toxic 5-lipoxygenase pathway inhibiting amount of a compound of Formula (IC) or a pharmaceutically acceptable salt thereof.

This invention also relates to a method of treating a 5-lipoxygenase pathway mediated disease in an animal in need thereof, provided that such animal is in need of treatment of a 5-lipoxygenase pathway mediated disease other than, or in addition to, rheumatoid arthritis, which comprises administering to such animal an effective, non-toxic 5-lipoxygenase pathway inhibiting amount of a compound of the formula

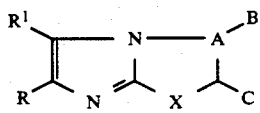

Formula (I)

wherein:
X is $CH_2$ or $S(O)n$;
n is 0, 1 or 2;
A is $CH_2$ or $CH_2CH_2$;
B and C are independently selected from H, methyl, ethyl or dimethyl;
$R^1$ and R are independently selected from
(a) pyridyl, provided that when either or both of R and $R^1$ are pyridyl X is other than $CH_2$;
(b) phenyl;
(c) monosubstituted phenyl wherein said substituent is selected from $C_{1-3}$ alkoxy, halo, $CF_3$, $C_{1-3}$ alkylthio, $C_{1-4}$ alkyl, 2,2,2-trihaloethoxy, prop-2-ene-1-oxy, $C_{1-3}$ alkylamino, $C_{1-3}$ dialkylamino, cyano, or N-(azacyclo $C_{5-6}$ alkyl);
(d) disubstituted phenyl wherein said substituents are independently selected from $C_{1-4}$ alkyl or $C_{1-3}$ alkoxy or the disubstituents together form a methylene dioxy group;
(e) 3,4,5-trimethoxyphenyl; provided that:
(1) when X is $CH_2$, both of R and $R^1$ are other than phenyl substituted in the 2 or 6 position with $C_{1-3}$ alkylamino; $C_{1-3}$ dialkylamino or N-(azacyclo $C_{5-6}$ alkyl);
(2) when X is $CH_2$, both of R and $R^1$ are other than pyridyl;
(3) when either of R or $R^1$ is cyanophenyl the other must be cyanophenyl or 4-pyridyl;
(4) when X is $S(O)_n$ and R or $R^1$ is phenyl substituted in the 2,3,5 or 6 position with $C_{1-3}$ alkylamino; $C_{1-3}$ dialkylamino or N-(azacyclo $C_{5-6}$ alkyl), the other must be 4-pyridyl);
or a pharmaceutically acceptable salt thereof.

This invention also relates to a compound of the formula

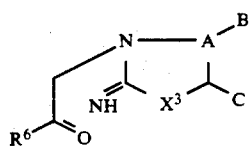

Formula (IIIA)

wherein:
$X^3$ is S;
A is $CH_2$ or $CH_2CH_2$;

B and C are independently selected from H, methyl, ethyl or dimethyl; and
$R^6$ is selected from:
(a) phenyl or monosubstituted phenyl wherein said substituent is selected from $C_{1-3}$ alkanamido, dialkylamino, N-(azacyclo $C_{5-6}$alkyl), halo, cyano, $C_{1-3}$ alkoxy, $C_{1-3}$ alkylthio, $C_{1-4}$ alkyl, $CF_3$ or H;
(b) disubstituted phenyl wherein said substituents are independently selected from $C_{1-4}$ alkyl or $C_{1-3}$ alkoxy, or the disubstituents together form a methylene dioxy group; or
(c) 3,4,5-trimethoxyphenyl;
provided that when A is $CH_2$ and B and C are H, $R^6$ is other than phenyl or monosubstituted phenyl wherein said substituent is halo, $C_{1-3}$ alkoxy, $C_{1-4}$ alkyl, $CF_3$ or $C_{1-3}$ alkylthio,
or a pharmaceutically acceptable salt thereof.

This invention also relates to a compound of the formula:

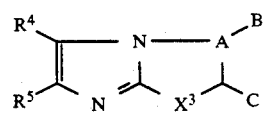

Formula (III)

wherein:
$X^3$ is $CH_2$ or S;
A is $CH_2$ or $CH_2CH_2$;
B and C are independently selected from H, methyl, ethyl or dimethyl; and
One of $R^4$ and $R^5$ must be H and the other is selected from:
(a) monosubstituted phenyl wherein said substituent is selected from $C_{1-3}$ alkanamido, N-($C_{1-3}$ alkyl)-$C_{1-3}$ alkanamido, amino, hydroxy, cyano, $C_{1-3}$ dialkylamino, N-(azacyclo $C_{5-6}$ alkyl), halo, $C_{1-3}$ alkoxy, $C_{1-3}$ alkylthio, $C_{1-4}$ alkyl, $CF_3$, prop-2-ene-1-oxy or 2,2,2-trihaloethoxy;
(b) disubstituted phenyl wherein said substituents are independently selected from $C_{1-4}$ alkyl or $C_{1-3}$ alkoxy, or the disubstituents together form a methylenedioxy group; or
(c) 3,4,5-trimethoxyphenyl; provided that:
(i) when $X^3$ is $CH_2$; $R^5$ must be H;
(ii) when A is $CH_2$, B and C are H, $X^3$ is S, and $R^4$ is H, $R^5$ is other than 2-, 3- or 4-methoxyphenyl, 2,4-dimethoxyphenyl, 4-hydroxyphenyl, 4-methylphenyl, 4-butylphenyl, 4-chlorophenyl or 4-bromophenyl; and
(iii) when A is $CH_2CH_2$, B and C are H, $X^3$ is S, and $R^4$ is H, $R^5$ is other than 4-bromophenyl, 4-chlorophenyl or 4-methylphenyl;
or a pharmaceutically acceptable salt thereof.

DETAILED DESCRIPTION OF THE INVENTION

As used herein, the term "Formula (IA)" will refer to compounds of the formula:

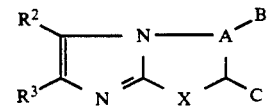

Formula (IA)

wherein:
X is $CH_2$ or $S(O)_n$;

n is 0, 1 or 2;
A is CH$_2$ or CH$_2$CH$_2$;
B and C are independently selected from H, methyl, ethyl or dimethyl;
R$^2$ and R$^3$ are independently selected from
  (a) pyridyl,
  (b) phenyl or monosubstituted phenyl wherein said substituent is selected from C$_{1-3}$ dialkylamino, C$_{1-3}$ alkylamino, N-(azacyclo C$_{5-6}$ alkyl), cyano, 2,2,2-trihaloethoxy, prop-2-ene-1-oxy, N-(C$_{1-3}$ alkyl)-(C$_{1-3}$ alkanamido), C$_{1-3}$ alkanamido, amino, hydroxy, C$_{1-3}$ alkylthio, C$_{1-4}$ alkyl, halo, or CF$_3$;
  (c) disubstituted phenyl wherein said substituents are independently selected from C$_{1-4}$ alkyl or C$_{1-3}$ alkoxy, or the disubstituents together form a methylenedioxy group; or
  (d) 3,4,5-trimethoxyphenyl; provided that:
    (1) when X is CH$_2$, both of R$^2$ and R$^3$ are other than pyridyl; and
    (2) when R$^3$ is cyanophenyl, R$^2$ must be either cyanophenyl or 4-pyridyl;
or a pharmaceutically acceptable salt thereof.

All the compounds of Formula (IA) can be prepared by the following synthetic route:

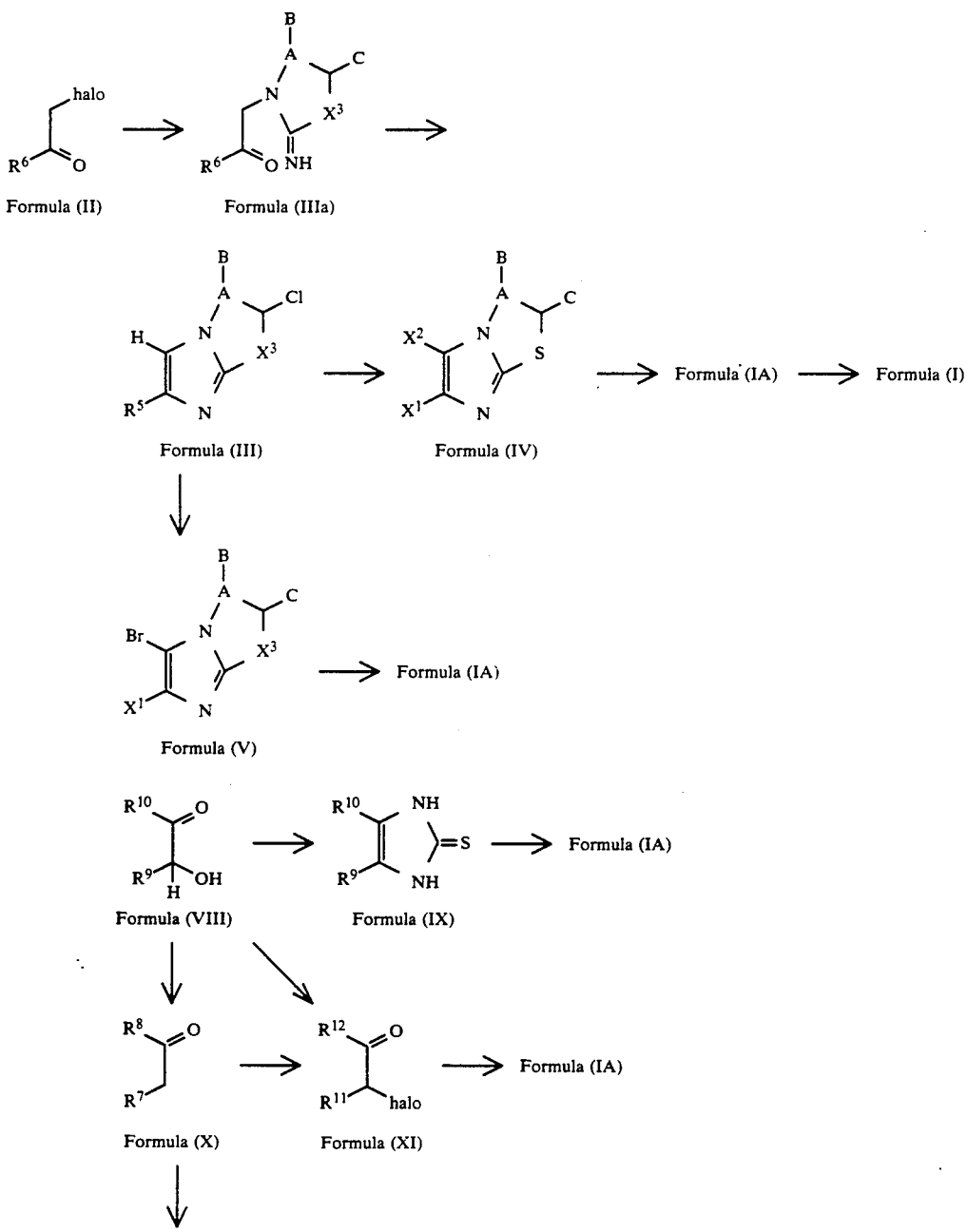

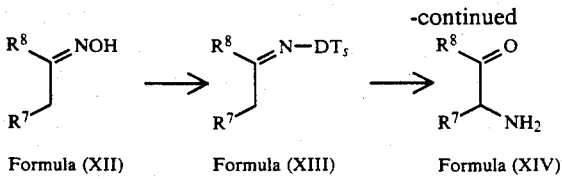

Formula (XII)  Formula (XIII)  Formula (XIV)

It will be apparent to one of skill in the art that all the compounds of Formula (I), Formula (IB) and Formula (IC) are encompassed by the scope of Formula (IA).

It will also be apparent to one of skill in the art that all of the compounds of Formula (IC) are embraced by the scope of Formula (I). All of the compounds of Formula (I) are useful as inhibitors of the 5-lipoxygenase pathway of arachidonic acid metabolism and some compounds of Formula (I) are also useful as intermediates in the production of compounds of Formula (I) and/or Formula (IB). All of the compounds of Formula (IB) are useful as inhibitors of the 5-lipoxygenase pathway of arachidonic acid metabolism and/or serve as intermediates in the production of compounds of Formula (IB) and/or Formula (I). All of the compounds of Formula (IC) are useful as inhibitors of the 5-lipoxygenase pathway of arachidonic acid metabolism and some compounds of Formula (IC) are also useful as intermediates in the production of compounds of Formula (I) and/or Formula (IB). All the compounds of Formula (III), Formula (IIIA) and Formula (V) are useful as intermediates in the production of compounds of Formula (I) and/or Formula (IB).

All the required compounds necessary to produce the compounds of Formula (IA), i.e., the compounds of Formulas (II), (IIIA), (III), (IV), (V), (VIII), (IX), (X), (XI), (XII), (XIII), (XIV) and (IA), can be obtained from commercial sources or can be prepared by techniques described herein. Moreover, any necessary compounds of Formula (V) and Formula (IIIA) where $X^3$ is $CH_2$ and of Formula (III) where $R^4$ is H can be prepared according to the method of Bender et al., U.S. Ser. No. 856,926, titled "Inhibitors of the 5-lipoxygenase pathway", filed simultaneously with this application; the disclosure of which is hereby incorporated by reference; and any necessary compounds of Formula (IV) and of Formula (V) where $X^3$ is S can be prepared according to the method of Bender et al., U.S. Ser. No. 856,246, titled "Process for preparing pyridyl-substituted imidazo [2,1-b] thiazoles and thiazines", filed simultaneously with this application, the disclosure of which is hereby incorporated by reference.

Compounds of Formula (IA) wherein X is S; A is $CH_2$ or $CH_2CH_2$; B and C are independently selected from H, methyl, or ethyl; and R and $R^1$ are independently mono, di or tri-substituted phenyl, are prepared from either (a) the corresponding Formula (IX) compounds or (b) the corresponding Formula (XI) compounds.

In the first procedure, the Formula (IX) compound is treated with the corresponding 1,2-dihaloethane or 1,3-dihalopropane and potassium carbonate by the method described by Bender et al, J. Med. Chem., 28, 1169 (1985) (therein designated as method B). The requisite Formula (IX) compounds wherein $R^9$ and $R^{10}$ are independently selected from (a) monosubstituted phenyl where said substituent is selected from $C_{1-3}$ dialkylamino, N-(azacyclo $C_{5-6}$ alkyl), $C_{1-3}$ alkoxy, 2,2,2-trihaloethoxy, prop-2-ene-1-oxy, $C_{1-4}$ alkyl, $C_{1-3}$ alkylthio, N-$C_{1-3}$ alkanamido, N-($C_{1-3}$ alkyl)-$C_{1-3}$ alkanamido, halo, H or $CF_3$, (b) disubstituted phenyl wherein said substitutents are independently selected from $C_{1-4}$ alkyl or $C_{1-3}$ alkoxy or the disubstitutents together form a methylenedioxy group, or (c) 3,4,5-trimethoxyphenyl are prepared by treating the corresponding Formula (VIII) compound with thiourea by the method described in Bender et al, ibid, (therein designated as the general method for preparation of 4,5-diarylimidazole-2-thiones). The Formula (VIII) compounds are prepared from the corresponding aryl carboxaldehydes employing the benzoin condensation catalyzed by cyanide (see, Ide et al., in "Organic Reactions", Wiley, (1948), Chapter 5) or the Stetter catalyst [Stetter et al., Synthesis, 733 (1975)].

Alternatively, compounds of Formula (IX) may be prepared from the corresponding ethanones of Formula (X) by reaction with hydroxylamine to afford the oximes of Formula (XII). Subsequent treatment of the Formula (XII) compounds with tosyl chloride and pyridine gives the oxime tosylates of Formula (XIII). Reaction of the Formula (XIII) compounds with strong base affords the 2-aminoethan-1-ones of Formula (XIV). Treatment of the Formula (XIV) compounds with sodium thiocyanate and hydrochloric acid by the method described in Ciba-Geigy AG., U.K. Patent Application Number GB 2,039,882 for the conversion of 2-phenyl-1-pyridyl-ethan-1-one into the 5-phenyl-4-pyridyl-2-mercaptoimidazole. The required ethanones of Formula (X) wherein $R^7$ and $R^8$ are independently selected from (a) monosubstituted phenyl where said substitutent is selected from $C_{1-3}$ alkoxy, 2,2,2-trihaloethoxy, prop-2-ene-1-oxy, $C_{1-4}$ alkyl, $C_{1-3}$ alkylthio, N-$C_{1-3}$ alkanamido, halo, H or $CF_3$, (b) disubstituted phenyl wherein said substituents are independently selected from $C_{1-4}$ alkyl or $C_{1-3}$ alkoxy or the disubstituents together form a methylenedioxy group, (c) 3,4,5-trimethoxyphenyl, or (d) $R^7$ and $R^8$ are both CN, are obtained by (a) Friedel-Crafts acylation of the substituted phenylacetyl chloride of the corresponding benzene, (b) Curtius rearrangement of the substituted stilbenecarbonyl azides derived from Perkin condensation of a substituted benzaldehyde with the substituted phenylacetic acid ester (by the method of Hill, et al., 13th Mid-American Regional Meeting of the American Chemical Society, March 1979; ORG 21), (c) reduction of the corresponding benzoin with zinc or tin by the method of Kohler et al., J. Amer. Chem. Soc., 52, 4133 (1930), and (d) Claisen condensation of a substituted phenylacetonitrile with a substituted aryl carboxylic acid ester (see, Magnani et al., Org. Syn. Coll., 3, 251 (1955).

In the second procedure for the preparation of Formula (IA) compounds wherein X is S; A is $CH_2$ or $CH_2CH_2$; B and C are independently selected from H, methyl or ethyl; and $R^3$ and $R^2$ are independently mono, di or trisubstituted, a 2-halo-ethan-1-one of Formula (XI) wherein $R^{11}$ and $R^{12}$ are independently selected from (a) monosustituted phenyl and said substitutent is selected from $C_{1-4}$ alkyl, halo (preferably chloro or bromo), H, $CF_3$, $C_{1-3}$ alkoxy, $C_{1-3}$ alkylthio, 2,2,2- trihaloethoxy, prop-2-ene-1-oxy, $C_{1-3}$ alkanamido, or (b) disubstituted phenyl wherein said substituents are independently selected from $C_{1-4}$ alkyl or $C_{1-3}$ alkoxy or the disubstituents together form a methylenedioxy group, is treated with a correspondingly substituted 2-amino-thiazoline or 2-amino-4,5-dihydro[1,3]thiazine by the method described in Bender, et al., *J. Med. Chem.*, 28, 1169 (1985) (therein designated as method A). The Formula (XI) compounds where halo is Br are prepared preferably by bromination of the corresponding Formula (X) compounds by the method described in Bender et al, ibid (therein designated as the general method for alpha-bromination of desoxybenzoins), or alternately the alpha-chloro Formula (XI) compounds are prepared from the corresponding Formula (VIII) compounds by treatment with $SOCl_2$ by the method of Fieser et al., *J. Org. Chem.*, 27, 2247 (1962).

Compounds of Formula (IA) where X is $CH_2$; A is $CH_2$ or $CH_2CH_2$; B and C are independently H, methyl or ethyl; and R and $R^1$ are both monosubstituted phenyl are prepared by the method described in Bender et al., U.S. Pat. No. 4,186,205, from the corresponding Formula (XI) compounds, prepared as described above, and the substituted 2-iminopyrrolidine or 2-iminopiperidine. The unsubstituted (B,C=H) and alkyl-substituted (B,C=$C_{1-3}$ alkyl) 2-iminopyrrolidines and piperidines are prepared by O-alkylation of the corresponding 2-pyrrolidones and 2-piperidones with dimethyl sulfate by the procedure of Wick et al., *Helv. Chim. Acta*, 54, 513 (1971), and subsequent treatment of the cyclic imidates with ammonium chloride in absolute alcohol by the method of Etienne et al., *Compt. Rend.*, 259, 2660 (1964). Unsubstituted 2-iminopyrrolidine and 2-iminopiperidine are preferably prepared from 4-chlorobutyronitrile and 5-chlorovaleronitrile, respectively as described by Moriconi et al., *J. Org. Chem.*, 33, 2109 (1968), as their hydrohalide salts and liberated to the free bases with concentrated aqueous sodium hydroxide.

Alternatively, compounds of Formula (IA) wherein X is $CH_2$ and R and $R^1$ are both monosubstituted phenyl are prepared from the corresponding Formula (V) compound wherein $X^3$ is $CH_2$ wherein $R^7$ and $R^8$ are independently selected from (a) monosubstituted phenyl where said substitutent is selected from $C_{1-3}$ alkoxy, 2,2,2-trihaloethoxy, prop-2-ene-1-oxy, $C_{1-4}$ alkyl, $C_{1-3}$ alkylthio, N-$C_{1-3}$ alkanamido, halo, H or $CF_3$, (b) disubstituted phenyl wherein said substituents are independently selected from $C_{1-4}$ alkyl or $C_{1-3}$ alkoxy or the disubstituents together form a methylenedioxy group, (c) 3,4,5-trimethoxyphenyl, or (d) $R^7$ and $R^8$ are both CN.

Treatment of the Formula (III) compounds wherein $X^3$ is $CH_2$ with bromine, by the procedure of Kano, *Yakugaku Zasshi*, 92, 51 (1972), results in bromination at the $R^3$ position to afford the compounds of Formula (V). Formula (III) compounds where $X^3$ is $CH_2$ are prepared in two steps from the corresponding Formula (IIIA) and Formula (II) compounds. The Formula (IIIA) compounds are prepared by treatment of the corresponding Formula (II) a-haloacetophenones with the appropriately substituted 2-iminopyrrolidine or 2-iminopiperidine in an inert solvent, such as chloroform or alcohol, and filtration of the product. Reflux of the Formula (IIIA) product in an aqueous or aqueous alcohol solvent until cyclodehydration is complete affords the Formula (III) compounds on neutralization with aqueous base. Compounds of Formula (V) wherein $X^3$ is $CH_2$ are obtained by bromination of the corresponding Formula (III) compounds, and are treated with n-butyl lithium (n-BuLi) in THF to afford 3-lithio derivatives by halogen-metal interchange. Transmetallation of the 3-lithio compounds with $MgBr_2$ affords the corresponding magnesium compounds, according to the method of Negishi et al., *J. Org. Chem.*, 42, 1821, (1977), which are coupled with the corresponding substituted bromobenzene in the presence of $PdCl_2$ (bis(diphenylphosphino)$C_{1-4}$ alkylene) catalyst using the method of Kumada et al., *Tetrahedron Letters*, 22, 5319 (1981), to afford the Formula (IA) compounds.

Compounds of Formula (IA) wherein X is S; A is $CH_2$ or $CH_2CH_2$; B and C are independently selected from H, methyl, or ethyl; and one of $R^2$ or $R^3$ is pyridyl and the other is mono-, di-, or trisubstituted phenyl are prepared from the corresponding Formula (IX) compounds by alkylation with the appropriate $C_{2-3}$ dihaloalkane and sodium hydride in DMF followed by addition of potassium carbonate and subsequent cyclization upon heating (using the procedure of Lantos et al., *J. Med. Chem.*, 27, 72 (1984) for the preparation of compounds 13 and 14 therein). The resulting two isomeric 6-aryl-5-pyridyl and 5-aryl-6-pyridyl Formula (IA) compounds are separated chromatographically (Lantos et al., cited above). The Formula (IX) compounds are prepared from either the corresponding (a) Formula (VIII) 2-hydroxy ethanones or (b) Formula (XIV) 2-amino ethanones. Formula (IX) compounds where at least one of $R^9$ or $R^{10}$ is pyridyl and the other is selected from (a) monosubstituted phenyl where said substituent is selected from $C_{1-3}$ alkoxy, 2,2,2-trihaloethoxy, prop-2-ene-1-oxy, $C_{1-4}$ alkyl, $C_{1-3}$ alkylthio, N-$C_{1-3}$ alkanamido, halo, H or $CF_3$, (b) disubstituted phenyl wherein said substitutents are independently selected from $C_{1-4}$ alkyl or $C_{1-3}$ alkoxy or the disubstitutents together form a methylenedioxy group, (c) 3,4,5-trimethoxyphenyl, or (d) pyridyl are prepared from the corresponding Formula (VIII) compounds by the same procedure as described above for the substituted diphenyl Formula (IX) compounds. Formula (VIII) compounds where one of $R^9$ or $R^{10}$ is 4-pyridyl are prepared by the method described in Bender et al., U.S. Pat. No. 4,175,127, by treatment of 4-pyridine carboxaldehyde cyanohydrin benzoate and a substituted benzaldehyde in t-butanol with sodium or potassium hydride.

Alternatively, pyridyl containing Formula (IX) compounds may be prepared from the corresponding Formula (X) ethanones in 4 steps by successive conversion of the Formula (X) compounds to the corresponding Formula (XII), Formula (XIII), and Formula (XIV) compounds by the method described in Ciba-Geigy AG., U.K. Patent Application Number GB 2,039,882, for the conversion of 2-phenyl-1-(3-pyridyl)-ethan-1-one into 5-phenyl-4-(3-pyridyl)-2-mercaptoimidazole. The requisite Formula (X) ethanones wherein U.S.S.N. at least one of $R^7$ and $R^8$ is pyridyl and the other is independently selected from (a) monosubstituted phenyl where said substitutent is selected from $C_{1-3}$ alkoxy, 2,2,2-trihaloethoxy, prop-2-ene-1-oxy, $C_{1-4}$ alkyl, $C_{1-3}$ alkylthio, N-alkanamido, halo, H or $CF_3$, (b) disubstituted phenyl wherein said substituents are independently selected from $C_{1-4}$ alkyl or $C_{1-3}$ alkoxy or the disubstituents together form a methylenedioxy group, or (c) 3,4,5-trimethoxyphenyl, are preferably prepared by Claisen condensation of a substituted phenylacetonitrile with a 2-, 3-, or 4-picolinic acid ester (see Cherkofsky et al., U.S. Pat. No. 4,199,592), or alternatively by reaction of the picolyl sodium or lithium and the appropriately substituted benzoic acid ester by the method described in Brust et al., Belgian Patent Number 668,701 (1966); *Chem. Abstr.*, 65, 5446c (1966).

The Formula (IA) compounds where both $R^2$ and $R^3$ are pyridyl and X is S are prepared in two steps from the corresponding Formula (VIII) 2-hydroxy-ethan-1-ones and the corresponding Formula (IX) compounds by the methods described above for the corresponding Formula (VIII), Formula (IX) and Formula (IA) compounds where the aryl groups are both substituted phenyl. The precursor dipyridyl Formula (VIII) compounds are prepared by the benzoin condensation as described above for the corresponding diphenyl Formula (VIII) compounds with the exception that thiourea must be added in the condensation of 4-pyridine carboxaldehyde.

Compounds of Formula (IA) where $R^1$ is 4-pyridyl and R is substituted phenyl are preferably prepared in two steps by the method described in Lantos et al., U.S. Ser. No. 737,137, filed May 29, 1985, the disclosure of which is hereby incorporated by reference, and the method described in Bender et al., U.S. Ser. No. 856,246, titled "Process for preparing pyridyl-substituted Imidazo [2,1-b] thiazoles and thiazines", which was filed simultaneously with this application, the disclosure of which is hereby incorporated by reference, from their corresponding Formula (III) and Formula (IV) compounds. The Formula IV compounds wherein A is $CH_2$ or $CH_2CH_2$, B and C are independently selected from H, methyl, ethyl, or dimethyl; $X^2$ is N-Z-carbonyl-1,4-dihydro-4-pyridyl, Z is $C_{1-8}$ alkyl, $C_{1-8}$ alkoxy, phenyl, phenoxy, benzyl or benzyloxy, and $X^1$ is (a) monosubstituted phenyl and said substituent is selected from H, $C_{1-3}$ alkoxy, halo, $CF_3$, $C_{1-3}$ alkylthio, $C_{1-4}$ alkyl, N-(azacyclo $C_{5-6}$ alkyl), N-($C_{1-3}$ alkyl)-($C_{1-3}$ alkanamido), $C_{1-3}$ dialkylamino, cyano, 2,2,2-trihaloethoxy prop-2-ene-1-oxy or disubstituted phenyl wherein said substituents are independently selected from $C_{1-4}$ alkyl or $C_{1-3}$ alkoxy or the disubstituents together form a methylene dioxy group, are prepared from the corresponding Formula (III) compounds. In the first step, the Formula (III) compound is treated at 5°–25° C. with pyridine and an acyl halide such as an alkylchloroformate (preferably ethylchloroformate) or an arylcarbonyl halide such as benzoylchloride in a solvent in which the reactants are soluble and inert, such as methylene chloride, to form the corresponding Formula (IV) compound. Compounds of Formula (IC) serve as intermediates in the preparation of the compounds of Formula (A). In the second step, the Formula (IV) compound, an N-acyldihydropyridine product, is deacylated and aromatized either with a mild oxidizing agent such as sulfur in refluxing decalin, tetralin or p-cymene or preferably with oxygen and excess potassium t-butoxide in t-butanol, to afford the compounds of Formula (A). The compounds of Formula (III) are prepared in two steps from the corresponding Formula (II) and Formula (IIIA) compounds by the method of Lantos et al., U.S. Ser. No. 737,137, cited above. Formula (IIIA) compounds are prepared by treatment of the appropriately substituted Formula (II) phenacyl halide with the correspondingly substituted 2-amino-3,4-dihydrothiazole or 2-amino-4,5-dihydro(1,3)thiazine in a chlorinated hydrocarbon or preferably an alcoholic solvent. The hydrohalide salt of the Formula (IIIA) compound which precipitates is refluxed in water or aqueous alcohol until cyclodehydration is complete. Neutralization with aqueous base affords the corresponding Formula (III) compound. The substituted Formula (IIIA) compounds are prepared from the corresponding acetophenones by treatment with bromine or alternatively prepared by acylating the corresponding mono- or disubstituted benzene by Friedel Crafts reaction with 2-chloroacetylchloride and $AlCl_3$, by the method of Joshi et al., *J. Het. Chem.*, 16, 1141 (1979).

The 2,2,2-trihaloethoxyphenyl and prop-2-en-1-oxyphenyl Formula (IA), Formula (III), and Formula (V) compounds are prepared by alkylation of the corresponding Formula (IA), Formula (III), and Formula (V) hydroxyphenyl compounds with a 2,2,2-trihaloalkylester of trifluoromethane sulfonic acid and 2-propenyl bromide respectively by the method described in Bender et al., *J. Med. Chem.*, 28, 1169–1177 (1985) for the preparation of compounds No. 23 and 33 described therein. The hydroxyphenyl Formula (IA), Formula (III), and Formula (V) compounds are prepared by treatment of the corresponding methoxyphenyl compounds with HBr in refluxing acetic acid or alternatively with $BBr_3$ in $CH_2Cl_2$. N-($C_{1-3}$ alkanamido) and N-($C_{1-3}$ alkyl)-N-($C_{1-3}$ alkanamido) phenyl substituted acetophenones, and in some cases the Formula (III), and Formula (IA) compounds, are prepared by acylation of the corresponding amino and N-($C_{1-3}$ alkylamino) compounds with the alkanoic acid anhydride or chloride in pyridine. Another alternative preparation of the N-($C_{1-3}$ alkyl)-N-($C_{1-3}$ alkanamido) phenyl carboxaldehydes, substituted Formula (III) and Formula (IA) compounds employs the alkylation of the corresponding N-($C_{1-3}$ alkanamido) phenyl substituted carboxaldehydes, Formula (III) and Formula (IA) compounds with sodium hydride and a $C_{1-3}$ alkyl bromide or iodide in dimethyl formamide.

Aminophenyl substituted Formula (III) and Formula (IA) compounds are prepared by hydrolysis of the corresponding N-($C_{1-3}$ alkanamido) compounds in refluxing 6N mineral acid.

N-($C_{1-3}$ alkylamino) phenyl substituted Formula (III), Formula (V), and Formula (IA) compounds are preferably prepared by acid catalyzed hydrolysis of the corresponding N-($C_{1-3}$ alkyl)-N-($C_{1-3}$ alkanamido) compounds as described above for the aminophenyl substituted compounds, or alternatively by reduction of the corresponding N-($C_{1-3}$ alkanamido) phenyl Formula (III), Formula (V) or Formula (IA) compounds with borane or borane dimethylsulfide complex in THF by the method of Brown, "Organic Synthesis via Boranes", John Wiley and Sons, (1975).

N,N-($C_{1-3}$ dialkylamino) phenyl substituted Formula (III) and Formula (IA) compounds were alternatively prepared by reduction of the corresponding N-($C_{1-3}$ alkyl)-N-($C_{1-3}$ alkanamido) compounds with borane as described above for the N-($C_{1-3}$ alkylamino) phenyl substituted compounds.

N-(azacyclo $C_{5-6}$ alkyl) phenyl substituted Formula (III) and Formula (IA) compounds are alternatively prepared by cyclodialkylation of the corresponding aminophenyl compounds with dibromobutane or dibromopentane and anhydrous potassium carbonate in an inert solvent such as dimethylformamide.

Compounds of Formula (I) where X is $S(O)_n$ and n is 1 or 2 are prepared by oxidation with one or two equivalents of an organic peracid as described in Bender et al., U.S. Pat. No. 4,263,311 and Bender et al., U.S. Pat. No. 4,175,127.

Compounds of Formula (I) where at least one of R and R¹ is pyridyl, X is S(O)$_n$ and n=2 are preferably prepared by oxidation of 1 equivalent of an acid salt of X=S(O)$_n$, n is 1, with ⅔ equivalent of an aqueous solution of KMnO4 according to the method of Chatterway et al., *J. Chem. Soc.*, 1352 (1930).

Compounds of Formula (I) where X is S(O)$_n$, n is 1 or 2, and where at least one of R¹ and R is C$_{1-3}$ alkylaminophenyl, C$_{1-3}$ dialkylaminophenyl, or N-(azacyclo C$_{5-6}$ alkyl)phenyl are preferably prepared by treating the immediate precursor alkanamidophenyl compound with an oxidizing agent (as described above for preparation of compounds of Formula (I) where X is S(O)$_n$ and n is 1 or 2) followed by hydrolysis of the alkanamide to the primary or secondary amine. The primary or secondary amine may then be further alkylated as described above to afford the tertiary amine S(O)$_n$ compounds where n is 1 or 2.

Pharmaceutically acceptable salts and their preparation are well known to those skilled in pharmaceuticals. Pharmaceutically acceptable salts of the compounds of Formula (IA) and the corresponding compounds of Formula (III), Formula (IIIA) and Formula (V) which are useful in the present invention include, but are not limited to, maleate, fumarate, lactate, oxalate, methanesulfonate, ethane-sulfonate, benzenesulfonate, tartrate, citrate, hydrochloride, hydrobromide, sulfate and phosphate salts. The preparation of such salts of some of the compounds of Formula (IA) is disclosed in Bender et al., U.S. Pat. No. 4,175,127; Bender et al., U.S. Pat. No. 4,263,311; Baetz, U.S. Pat. No. 4,110,460; Ciba Geigy, U.K. Patent Application No. GB 2,039,882-A; and Bender et al., U.S. Pat. No. 4,186,205, the disclosures of all of which are hereby incorporated by reference, and such disclosures are also relevant to the preparation of the pharmaceutically acceptable salts of Formula (III), Formula (IIIA) and Formula (V) compounds. Preferred pharmaceutically acceptable salts of the compounds of Formula (IA) include the hydrochloride and hydrobromide salts.

Some of the compounds of Formula (IA) can form covalent hydrates i.e., the compounds of Formula (IA) where R³ is other than pyridyl, R² is 2- or 4-halo, CF₃ or cyano substituted phenyl and X is S will form covalent hydrates where an OH group is attached to the carbon atom attached to R³ and an H is attached to the carbon atom attached to R². The preparation of such hydrates is disclosed by Bender et al., U.S. Pat. No. 4,153,706, issued May 8, 1979, the disclosure of which is hereby incorporated by reference, which claims compounds of the formula

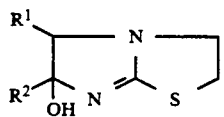

wherein R¹ is 4-substituted phenyl wherein said substituent is selected from lower alkoxy, lower alkylthio, fluoro, chloro, bromo or trifluoro methyl; and R² is 4-substituted phenyl wherein said substituent is an electron withdrawing group, in particular, fluoro, chloro, bromo or trifluoromethyl. At least some of the hydrates disclosed by Bender et al. have 5-lipoxygenase inhibiting activity as determined by the assays set forth in the Examples. Therefore, the scope of the compounds of Formula (IA) includes such hydrates, described in Bender et al., which have 5-lipoxygenase pathway inhibiting activity or which are useful to prepare other compounds of Formula (IA) which have 5-lipoxygenase pathway inhibiting activity.

It is known that some of the compounds of Formula (I) are useful for inhibiting the cyclooxygenase pathway of arachidonic acid metabolism. It has now been discovered that all the compounds of Formula (I) are useful for treating disease states mediated by the 5-lipoxygenase pathway of arachidonic acid metabolism by inhibiting such pathway. The discovery that the compounds of Formula (I) are inhibitors of the 5-lipoxygenase pathway or are dual inhibitors of the cyclooxygenase and 5-lipoxygenase pathways is based on the effects of the compounds of Formula (I) on tissue inflammation in vivo and on the production of cyclooxygenase products and 5-lipoxygenase products by inflammatory cells in vitro in assays which are described in the Examples. In summary, such assays reveal that the compounds of Formula (I) inhibit the infiltration of polymorphonuclear leukocytes into inflammatory lesions in mice (carrageenan-induced peritonitis) and rats (air pouch inflammation induced by arachidonic acid). In addition, the compounds of Formula (I) display anti-inflammatory activity in arachidonic acid-induced inflammation in the mouse ear and rat paw models. The cyclooxygenase inhibitor, indomethacin, did not reduce inflammation or cell infiltration in these assays. These data, together with previous observations on the anti-edematous effects of the compounds of Formula (I) in inflammatory lesions caused by cyclooxygenase-generated products, reveal that the compounds of Formula (I) inhibit either the 5-lipoxygenase pathway or both the 5-lipoxygenase and cyclooxygenase pathways of arachidonic acid metabolism. The 5-lipoxygenase pathway inhibitory action of the compounds of Formula (I) was confirmed by showing that such compounds (a) impaired the production of 5-lipoxygenase products such as leukotriene B₄ (di-HETE) and 5-HETE production by RBL-1 cells, (b) impaired the production of LTC₄ by human monocytes, and (c) that peritoneal exudate cells harvested from Formula (I) compound treated mice exhibited a reduced capacity to produce LTB₄ in vitro.

The pathophysiological role of arachidonic acid metabolites has been the focus of recent intensive studies. In addition to the well-described phlogistic activity (i.e. general inflammatory activity) of prostaglandins, the more recent description of similar activity for eicosanoids has broadened the interest in these products as mediators of inflammation [See, O'Flaherty, *Lab. Invest.*, 47, 314–329 (1982)]. The reported discovery of potent chemotactic and algesic activity for LTB₄ [see, Smith, *Gen. Pharmacol.*, 12, 211–216 (1981) and Levine et al., *Science*, 225, 743–745 (1984)], together with known LTC₄ and LTD₄-mediated increase in capillary permeability [see, Simmons et al., *Biochem. Pharmacol.*, 32, 1353–1359 (1983), Veno et al., *Prostaglandins*, 21, 637–647 (1981), and Camp et al., *Br. J. Pharmacol.*, 80, 497–502 (1983)], has led to their consideration as targets for pharmacological intervention in both the fluid and cellular phases of inflammatory diseases.

The pharmacology of several inflammatory model systems has attested to the effectiveness of corticosteroids in reducing the cellular infiltration. These results, and the observation that corticosteroids inhibit the generation of both cyclooxygenase and lipoxygenase products, suggest that such dual inhibitors may effectively reduce both the fluid and cellular phases of the inflammatory response since selective cyclooxygenase inhibitors do not reliably inhibit cell influx into inflammatory sites [See, Vinegar et al., *Fed. Proc.*, 35, 2447-2456 (1976), Higgs et al., *Brit. Bull.*, 39, 265-270 (1983), and Higgs et al., *Prostaglandins, Leukotrienes and Medicine*, 13, 89-92 (1984)]. The observations outlined above cogently argue that a dual inhibitor of arachidonic acid metabolism would be a more effective anti-inflammatory agent than an inhibitor of cyclooxygenase only. Under optimal conditions, it is likely that an agent with preferential lipoxygenase inhibitory activity would not share the ulcerogenic liability of cyclooxygenase inhibitors or the toxicity of corticosteroids.

Recent clinical data also support the enthusiasm for dual inhibitors of arachidonic acid metabolism in a variety of inflammatory diseases in which granulocyte and-/or monocyte infiltration is prominent. The reported demonstration of elevated levels of $LTB_4$ in rheumatoid arthritic joint fluid [See, Davidson et al., *Ann. Rheum. Dis.*, 42, 677-679 (1983)] also suggests a contributing role for arachidonic acid metabolites in rheumatoid arthritis. The recently reported preliminary observation of efficacy, including remission, reported with sulfasalazine treatment of rheumatoid arthritic patients [See Neumann et al., *Brit. Med. J.*, 287, 1099-1102 (1983)] illustrates the utility of inhibitors of the 5-lipoxygenase pathway in *rheumatoid arthritis*.

Sulfasalazine, which is used for treatment of ulcerative colitis, has been reported to inhibit $LTB_4$ and 5-HETE production in vitro [See, Stenson et al., *J. Clin. Invest.*, 69, 494-497 (1982)]. This observation, coupled with the fact that it has been reported that inflamed gastrointestinal mucosa from inflammatory bowel disease patients showed increased production of $LTB_4$ [See, Sharon et al., *Gastroenterol.*, 84, 1306 (1983)], suggests that sulfasalazine can be effective by virtue of inhibition of production of chemotactic eicosanoids (such as the 5-lipoxygenase pathway product known as $LTB_4$). The observations serve to underscore utility of inhibitors of the 5-lipoxygenase pathway in inflammatory bowel disease.

Another area of utility for an inhibitor of the 5-lipoxygenase pathway is in the treatment of psoriasis. It was demonstrated that involved psoriatic skin had elevated levels of $LTB_4$ [See, Brain et al., *Lancet*, 19, Feb. 19, 1983]. The promising effect of benoxaprofen on psoriasis [See, Allen et al., *Brit. J. Dermatol.*, 109, 126-129 (1983)], a compound with in vitro lipoxygenase inhibitory activity on psoriasis, lends support to the concept that 5-lipoxygenase pathway inhibitors can be useful in the treatment of psoriasis.

Lipoxygenase products have been identified in exudate fluids from gouty patients. This disorder is characterized by massive neutrophil infiltration during the acute inflammatory phases of the disease. Since a major 5-lipoxygenase product, $LTB_4$, is produced by neutrophils, it follows that inhibition of the synthesis of $LTB_4$ can block an amplification mechanism in gout.

Another area in which inhibitors of the 5-lipoxygenase pathway can have utility is in myocardial infarction. Studies in dogs with the dual cyclooxygenase and 5-lipoxygenase inhibitor, BW755-C, demonstrated that the area of infarction following coronary occlusion was reduced, and such reduction was attributed to inhibition of leukocyte infiltration into the ischaemic tissue [See, Mollane et al., *J. Pharmacol. Exp. Therap.*, 228, 510-522 (1984)].

Yet another area of utility for inhibitors of the 5-lipoxygenase pathway is in the area of prevention of rejection of organ transplants. [See, e.g., Foegh et al., *Adv. Prostaglandin, Thromboxane, and Leukotriene Research*, 13, 209-217 (1983)].

Furthermore, another area of utility for inhibitors of the 5-lipoxygenase pathway is in the treatment of inflammatory reaction in the central nervous system, including multiple sclerosis. [See, e.g., MacKay et al., *Clin. Exp. Immunol.*, 15, 471-482 (1973)]. Formula (I) compounds, but not indomethacin, show efficacy in inhibiting experimental allergic encephalomyelitis (EAE) in rats.

Yet another utility for inhibitors of the 5-lipoxygenase pathway is in the treatment of tissue trauma. [See, e.g., Denzlinger et al., *Science*, 230 (4723), 330-332 (1985)].

A further area of utility for inhibitors of the 5-lipoxygenase pathway is in the treatment of asthma. [See, e.g., Ford-Hutchinson, *J. Allerg. Clin. Immunol.*, 74, 437-440 (1984)].

Compounds of Formula (I) which are preferred because of their potent 5-lipoxygenase pathway inhibiting activity, as evidenced by their ability to inhibit the 5-lipoxygenase products known as 5-HETE, $LTB_4$ and-/or $LTC_4$, are listed in Table A, below.

This invention also relates to a pharmaceutical composition comprising a pharmaceutically acceptable carrier or diluent and an effective, 5-lipoxygenase pathway inhibiting amount of a compound of Formula (IC) or a pharmaceutically acceptable salt thereof.

The compounds of Formula (I) and (IC) are administered in conventional dosage forms prepared by combining a therapeutically effective amount (i.e., a 5-lipoxygenase pathway inhibiting amount) of a compound of Formula (I) or (IC) ("active ingredient") with standard pharmaceutical carriers or diluents according to conventional procedures. These procedures may involve mixing, granulating and compressing or dissolving the ingredients as appropriate to the desired preparation.

TABLE A

Formula (I)

| Compound Number | $R^1$ | R | X | A | n |
|---|---|---|---|---|---|
| 3 | 4-(pyrrolidin-1-yl)phenyl | 4-(pyrrolidin-1-yl)phenyl | $S(O)_n$ | $CH_2$ | 0 |
| 6 | 4-fluorophenyl | 4-dimethylaminophenyl | $S(O)_n$ | $CH_2$ | 0 |
| 9 | 4-diethylaminophenyl | 4-diethylaminophenyl | $S(O)_n$ | $CH_2$ | 0 |
| 14 | 4-fluorophenyl | 4-methoxyphenyl | $S(O)_n$ | $CH_2$ | 0 |
| 17 | 4-ethylaminophenyl | 4-ethylaminophenyl | $S(O)_n$ | $CH_2$ | 0 |
| 24 | 4-pyridyl | 4-(pyrrolidin-1-yl)phenyl | $S(O)_n$ | $CH_2$ | 0 |
| 27 | 4-pyridyl | 4-fluorophenyl | $S(O)_n$ | $CH_2$ | 1 |

TABLE A-continued

Formula (I)

$$\underset{R}{\overset{R^1}{>}}=\underset{N}{\overset{N-A-B}{\underset{X}{\bigvee}}}C$$

| Compound Number | R¹ | R | X | A | n |
|---|---|---|---|---|---|
| 28 | 4-pyridyl | 4-fluorophenyl | S(O)n | CH₂ | 2 |
| 1 | 4-pyridyl | 4-fluorophenyl | S(O)n | CH₂ | 0 |
| 2 | 4-pyridyl | 4-(1-propylamino)phenyl | S(O)n | CH₂ | 0 |
| 4 | 4-(piperidin-1-yl)phenyl | 4-(piperidin-1-yl)phenyl | S(O)n | CH₂ | 0 |
| 7 | 3,4-(methylenedioxy)phenyl | 4-pyridyl | CH₂ | CH₂ | — |
| 15 | 4-trifluoromethylphenyl | 4-trifluoromethylphenyl | S(O)n | CH₂ | 0 |
| 16 | 3,4-(methylenedioxy)phenyl | 3,4-(methylenedioxy)phenyl | S(O)n | CH₂ | 0 |
| 17 | 4-ethylaminophenyl | 4-ethylaminophenyl | S(O)n | CH₂ | 0 |
| 18 | 4-pyridyl | 4-methoxyphenyl | S(O)n | CH₂ | 0 |
| 19 | 4-fluorophenyl | 4-fluorophenyl | S(O)n | CH₂ | 0 |
| 21 | 4-methoxyphenyl | 4-methoxyphenyl | S(O)n | CH₂ | 0 |
| 20 | 4-methoxyphenyl | 4-methoxyphenyl | S(O)n | CH₂CH₂ | 0 |
| 22 | 4-methoxyphenyl | 4-methoxyphenyl | CH₂ | CH₂ | — |
| 11 | 4-pyridyl | 4-pyridyl | S(O)n | CH₂ | 0 |

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of atroche or lozenge. The amount of solid carrier will vary widely but preferably will be form about 25 mg. to about 1 g. If a liquid carrier is used, the preparation will be in the form of a syrup, emulsion, soft gelatin capsule, sterile injectable liquid such as an ampule or nonaqueous liquid suspension.

To obtain a stable water soluble dose form, a pharmaceutically acceptable salt of a compound of Formula (I) or (IC) is dissolved in an aqueous solution of an organic or inorganic acid, such as a 0.3M solution of succinic acid, or, preferably, citric acid.

Preferably, each parenteral dosage unit will contain the active ingredient in an amount of from about 50 mg. to about 500 mg. Preferably each oral dosage unit will contain the active ingredient in an amount of from about 100 mg to about 1,000 mg.

This invention relates to a method of treating a disease state which is mediated by the 5-lipoxygenase pathway in an animal in need thereof, including humans and other mammals, provided that such animal is in need of treatment of a 5-lipoxygenase pathway mediated disease other than, or in addition to, rheumatoid arthritis, which comprises administering to such animal an effective, 5-lipoxygenase pathway inhibiting amount of a Formula (I) compound or a pharmaceutically acceptable salt thereof. By the term "treating" is meant prophylactic or therapeutic therapy. By the term "mediated" is meant caused by or exacerbated by. This invention also relates to a method of treating rheumatoid arthritis in a animal in need thereof, including humans and other mammals, which comprises administering to such animal an effective, 5-lipoxygenase pathway inhibiting amount of a compound of Formula (IC) or a pharmaceutically acceptable salt thereof. By the term "treating" is meant prophylactic or therapeutic therapy. The Formula (I) compound is administered to an animal in need of treatment of a 5-lipoxygenase pathway mediated disease state, other than or in addition to rheumatoid arthritis, in an amount sufficient to inhibit the 5-lipoxygenase pathway. The Formula (IC) compound is administered to an animal in need of treatment of rheumatoid arthritis in an amount sufficient to inhibit the 5-lipoxygenase pathway. Such Formula (I) or (IC) compound can be administered to such animal in a conventional dosage form prepared by combining the Formula (I) or (IC) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. As stated above, it will be apparent to one of skill in the art that all the compounds of Formula (IC) are embraced by the scope of Formula (I), and as such, all the following disclosure regarding appropriate pharmaceutical composition dosage forms and preferred dosage ranges are applicable to both Formula (I) and Formula (IC) compounds which will hereafter be collectively referred to as "Formula (I)" compound(s). The route of administration of the Formula (I) compound may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred. The daily parenteral dosage regimen for a compound will preferably be from about 50 mg to about 1,000 mg per day. The daily oral dosage regimen will preferably be from about 150 mg to about 2,000 mg.

The compounds for Formula (I) may also be administered by inhalation. By "inhalation" is meant intranasal and oral inhalation administration. Appropriate dosage forms for such administration, such as an aerosol formulation or a metered dose inhaler, may be prepared by conventional techniques. The preferred daily dosage amount of a compound of Formula (I) administered by inhalation is from about 10 mg to about 100 mg per day.

The compounds of Formula (I) may also be administered topically to a mammal in need of the inhibition of the 5-lipoxygenase pathway of arachidonic acid metabolism. Thus, the compounds of Formula (I) may be administered topically in the treatment of inflammation in an animal, including man and other mammals, and may be used in the relief of rheumatoid arthritis, rheumatoid spondylitis, osteoarthritis, gouty arthritis and other arthritic conditions, inflammed joints, eczema, psoriasis or other inflammatory skin conditions such as sunburn; inflammatory eye conditions including conjunctivitis; pyresis, pain and other conditions associated with inflammation.

The amount of a compound of Formula (I) (hereinafter referred to as the active ingredient) required for therapeutic effect on topical administration will, of course, vary with the compound chosen, the nature and severity of the inflammatory condition and the animal undergoing treatment, and is ultimately at the discretion of the physician. A suitable anti-inflammatory dose of an active ingredient is 0.5 mg to 500 mg of base per kilogram bodyweight for topical administration, the most preferred dosage being 0.5 to 50 mg/kg of animal bodyweight, for example 5 to 25 mg/kg; administered two or three times daily. For application to the skin, from 1 $\mu$g to several mg of active ingredient may be applied per application, preferably from 10 to 100 $\mu$g per application.

By topical administration is meant non-systemic administration and includes the application of a compound of Formula (I) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefore and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as prolylene glycol or macrogols. The formulation may incorporate any suitable surface active agent such as an anionic, cationic or non-ionic sulfactant such as sorbitan esters or polyoxyethylene derivatives thereof. Suspending agents such as natural gums, cellulose derivatives or inorganic materials such as silicaceous silicas, and other ingredients such as lanolin, may also be included.

It will be recognized by one of skill in the art that the optimal quantity and spacing of individual dosages of the Formula (I) compound will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of the Formula (I) compound given per day for a defined number of days, can be ascertained by those skilled in the art using conventional course of treatment determination tests.

EXAMPLES

Without further elaboration, it is believed that one skilled in the art can, using the preceding description, utilize the present invention to its fullest extent. The following examples are, therefore, to be construed as merely illustrative and not a limitation of the scope of the present invention in any way.

As used herein, the term "Compound 1" refers to the compound of Formula (I) wherein $R^1$ is 4-pyridyl, R is 4-fluorophenyl, A is $CH_2$, X is $S(O)n$, and n is 0.

Temperature is in degrees Centigrade (°C.).

SYNTHESIS EXAMPLES

EXAMPLE 1

5,6-bis(4-N,N-diethylaminophenyl)-2,3-dihydroimidazo[2,1-b]thiazole, Formula (I) compound Compounds of Formula (I) wherein X is S; A is $CH_2$ or $CH_2CH_2$; B and C are independently selected from H, methyl, or ethyl; and R and $R^1$ are independently mono, di or tri-substituted phenyl, are prepared by the method described in Bender et al., U.S. Pat. No. 4,263,311, and Bender et al., *J. Med. Chem.*, 28, 1169-1177 (1985). Reduction of 6-(alkanamidophenyl) compounds with two to three equivalents of borane or borane-dimethylsulfide complex in tetrahydrofuran at room temperature affords the 6-(N-alkylaminophenyl) derivatives. Using this procedure, 5,6-bis(4-N-ethylacetamidophenyl)-2,3-dihydroimidazo(2,1-b)thiazole, prepared as described in Bender et al., ibid, was reduced to 5,6-bis(4-diethylaminophenyl)-2,3-dihydroimidazo[2,1-b]thiazole by employing 6 equivalents of borane-dimethylsulfide complex by the method of Brown et al., *J. Org. Chem.*, 38, 2786 (1973). This product was isolated by chromatography on alumina (methylene chloride:chloroform, 1:1) and recrystallized from methanol. It had a melting point (mp) of 168°-169° C., and was analyzed for $C_{25}H_{32}N_4S$; Calcd.: C, 71.39; H, 7.67; N, 13.32; Found: C, 71.38; H, 7.72; N, 13.31.

EXAMPLE 2

5,6-bis(4-(1-piperidinyl)phenyl)-2,3-dihydroimidazo[2,1-b] thiazole, Formula (I) compound A mixture of 1.3 g (4.2 mmoles) of 5,6-bis(4-aminophenyl)-2,3-dihydroimidazo[2,1-b]thiazole, prepared as described in Bender et al., *J. Med. Chem.*, 28, 1169-1177 (1985), 2.2 g (9.7 mmoles) of 1,5-dibromopentane, and 2.7 g (19.4 mmoles) of powdered potassium carbonate in 25 ml of dry DMF was heated to reflux for 1 hour. Another 2.7 g of powdered potassium carbonate and 2.2 g of 1,5-dibromopentane were added and refluxed for an additional 2 hours. Water was added and the mixture acidified and washed with $CH_2Cl_2$. The aqueous phase was made alkaline and the product extracted into $CH_2Cl_2$. The organic phase was dried over potassium carbonate and concentrated in vacuo. The residue was column chromatographed on silica and the product eluted with $CH_3CN$—$CH_2Cl_2$ (1:1). The solvent was removed in vacuo, and the residue was dissolved in methanol. Addition of ethereal HCl gave the title Formula (I) compound, mp 280°-285° C. Analyzed for $C_{27}H_{32}N_4S.3HCl.1H_2O$, Calculated, C: 56.58, H: 6,25, N: 9.84; Found, C: 56.69, H: 5.99, N: 9.79.

EXAMPLE 3

5,6-bis(4-(1-pyrrolidinyl)phenyl)-2,3-dihydroimidazo[2,1-b] thiazole, Formula (I) compound A mixture of 1.3 g (4.2 mmoles) of 5,6-bis(4-aminophenyl)-2,3-dihydroimidazo(2,1-b)thiazole, prepared as described in Example 2, 2.1 g (9.7 mmoles) of 1,4-dibromobutane, and 2.7 g (19.4 mmoles) of powdered potassium carbonate in 25 ml of dry DMF was refluxed for 2 hours under argon. The reaction mixture was poured into water, acidified and washed with $CH_2Cl_2$. The aqueous phase was made basic and extracted with $CH_2Cl_2$. The organic layer was dried over potassium carbonate, concentrated and column chromatographed on silica, eluting the product with ethyl acetate/$CH_2Cl_2$ (2:10). The solvent was evaporated and the solid residue recrystallized from $CH_2Cl_2$—$CH_3OH$ to afford the title Formula (I) compound, mp 235°-237° C. Analyzed for $C_{25}H_{28}N_4S.CH_3OH$, Calculated, C; 69.60, H: 7.19, N: 12.49; Found, C: 69.53, H: 7.01, N: 12.68.

EXAMPLE 4

5-(4-Dimethylaminophenyl)-6-(4-fluorophenyl)-2,3-dihydroimidazo[2,1-b]-thiazole and
6-(4-dimethylaminophenyl)-5-(4-fluorophenyl)-2,3-dihydroimidazo[2,1-b]thiazole, Formula (I) compounds A solution of 0.40 g (1.28 mmoles) of 4-(4-dimethylaminophenyl)-5-(4-fluorophenyl)-2-mercaptoimidazole, a Formula (IV) compound, [obtained by treatment of the corresponding Formula (VIII) compound (prepared from 4-dimethylaminobenzaldehyde and 4-fluorobenzaldehyde as described by Ide et al., in and "Organic Reactions"; John Wiley and Sons, (1948) Chapter 5) with thiourea in DMF by the method described in Bender et al., *J. Med. Chem.*, 28, 1169 (1985) (therein designated as the general method for preparation of 4,5-diarylimidazole-2-thiones)] in 15 ml of dry DMF was treated with 0.061 g (1.28 mmoles) of a 50% sodium hydride dispersion. 0.18 g (1.28 mmoles) of 1-bromo-2-chloroethane was added after 0.5 hours stirring at ambient temperature. After an additional 12 hours stirring, 0.18 g (1.28 mmoles) of powdered potassium carbonate was added, and the mixture heated to 150° C. for 2 hours. The solvent was removed in vacuo and the residue extracted with chloroform. The solution was washed with water, dried over $MgSO_4$ and concentrated in vacuo. Column chromatography on silica afforded two isomers eluting with 10% and 20% $CH_3CN$ in $CH_2Cl_2$. Evaporation of the solvents followed by recrystallization from methanol gave 5-(4-dimethylaminophenyl)-6-(4-fluorophenyl)-2,3-dihydroimidazo[2,1-b]thiazole, mp 163°-164.5° C., (TLC, silica, 10% $CH_3CN$ in $CH_2Cl_2$, Rf 0.17) and 6-(4-dimethylaminophenyl)-5-(4-fluorophenyl)-2,3-dihydroimidazo[2,1-b]thiazole, mp 195°-201° C., (TLC, silica, 10% $CH_2CN$ in $CH_2Cl_2$, Rf 0.3).

EXAMPLE 5

5-(2-pyridinyl)-6-(4-fluorophenyl)-2,3-dihydroimidazo[2,1-b]thiazole and
5-(4-fluorophenyl)-6-(2-pyridinyl)-2,3-dihydroimidazo[2,1-b]thiazole, Formula (I) compounds a) 1-(2-Pyridinyl)-2-(4-fluorophenyl)ethanone (Formula (X) compound)

To a solution of 40.8 g (0.60 mol) of sodium ethoxide in 200 ml absolute ethanol was added a mixture of 60.5 g (0.40 mol) of ethyl picolinate and 54.1 g (0.40 mol) of 4-fluorophenylacetonitrile. The solution was refluxed 10 minutes, then cooled to ambient temperature. The solids were dissolved by the addition of 330 ml of water. Then, 50 ml 12N hydrochloric acid was added dropwise. The solid was collected by filtration, washed with water, and dried overnight (30° C. in vacuo) to give 1-(2-pyridinyl)-2-cyano-2-(4-fluorophenyl)-ethen-1-ol. This compound was dissolved in 250 ml 48% hydrobormic acid and refluxed for 17 hours. Upon cooling, aqueous ammonium hydroxide was added until the reaction mixture was basic. The aqueous solution was extracted three times with chloroform. The combined organic extracts were washed with water, dried ($MgSO_4$), and concentrated. The resulting solid was chromatographed on silica gel with ether-petroleum ether (1:3) as eluant, and recrystallized from 2-propanol-hexane to give the title Formula (X) compound, m.p. 56.58° C.

b) 1-(2-Pyridinyl)-2-(4-fluorophenyl)ethanone, oxime (Formula (XII) compound)

A solution of 18.5 g (0.086 mol) of 1-(2-pyridinyl)-2-(4-fluorophenyl)-ethanone, prepared as described in part a, 52.7 g (0.387 mol) of sodium acetate trihydrate, and 19.6 g (0.282 mol) of hydroxylamine hydrochloride in 280 ml methanol-water (1:1) was refluxed for 1 hour. Upon cooling to 5° C., the precipitate was collected by filtration, washed with water, and dried overnight (30° C. in vacuo). The title Formula (XII) compound was recrystallized from methanol-water, m.p. 106° C.

c) 1-(2-Pyridinyl)-2-(4-fluorophenyl)ethanone, 0-[(4-methylphenyl)sulfonyl]oxime (Formula (XIII) compound)

To a solution of 19.6 g (0.085 mol) of 1-(4-pyridinyl)-2-(4-fluorophenyl)-ethanone, oxime, prepared as described in part b, in 100 ml of dry pyridine at 0° C. under argon was added 20.3 g (0.106 mol) of p-toluenesulfonyl chloride. The mixture was stirred at 25° C. for 20 hours, and then poured into ice/water. The solid was collected by filtration and dried (25° C. in vacuo to give the title Formula (XIII) compound, m.p. 120°-122° C.

d) 4-(2-Pyridinyl)-5-(4-fluorophenyl)imidazole-2-thione (Formula (IX) compound)

A suspension of 30.7 g (0.08 mol) of 1-(2-pyridinyl)-2-(4-fluorophenyl)-ethanone, 0-[(4-methylphenyl) sulfonyl]oxime, prepared as described in part c, in 170 ml absolute ethanol at 5° C. under argon was treated with a solution of 8.6 g (0.10 mol) of potassium ethoxide in 90 ml of absolute ethanol. The suspension was stirred at 5° C. for 1 hour. Then, 260 ml of ether was added, and the reaction mixture was stirred for an additional 90 minutes. The suspension was then filtered and washed with ether. The ethereal solution was washed four times with 10% hydrochloric acid. The combined aqueous acid extracts were concentrated in vacuo, then redissolved in 150 ml water. Then 15.5 g (0.16 mol) potassium thiocyanate was added, and the reaction was refluxed for 1 hour. After cooling, the reaction mixture was poured into 5% sodium bicarbonate solution. The solid was collected by filtration and dried overnight (30° C. in vacuo) to give the title Formula (IX) compound, m.p. 248°-250° C.

e)
5-(2-Pyridinyl)-6-(4-fluorophenyl)-2,3-dihydroimidazo [2,1-b]thiazole
5-(4-fluorophenyl)-6-(2-pyridinyl)-2,3-dihydroimidazo[2,1-b]thiazole (Formula (I) compounds)

A solution of 9.76 g (0.036 mol) of 4-(2-pyridinyl)-5-(4-fluorophenyl)-imidazole-2-thione, prepared as described in part d, in 250 ml of dry N,N-dimethylformamide was treated with 3.52 g (0.073 mol) of a 50% oil dispersion of sodium hydride. The solution was stirred for 30 minutes, followed by the addition of 13.95 g (0.074 mol) of 1,2-dibromoethane. The reaction mixture was stirred for 3 hours, and then poured into ice/water. The aqueous suspension was extracted several times with methylene chloride. The combined organic layers were washed with water, dried (MgSO$_4$), and concentrated. The products were separated by chromatography on silica gel with 10% acetonitrile in methylene chloride and 25% acetonitrile in methylene chloride as eluants. Each product was recrystallized from acetonitrile-hexane to give the title Formula (I) compounds 5-(2-pyridinyl)-6-(4-fluoro-phenyl)-2,3-dihydroimidazo[2,1-b]thiazole, m.p. 152°-154° C., and 5-(4-fluorophenyl)-6-(2-pyridinyl)-2,3-dihydroimidazo[2,1-b]thiazole, m.p. 164°-166° C.

EXAMPLE 6

6-(4-pyridyl)-5-(3,4-methylenedioxyphenyl)-2,3-dihydroimidazo [2,1-b]thiazole and
4-(4-pyridyl)-6-(3,4-methylenedioxyphenyl)-2,3-dihydroimidazo [2,1-b]thiazole (Formula (I) compounds)

The compounds of Formula (I) described in Example 5, as well as monosubstituted phenyl compounds of Formula (I) where the phenyl substituent is $C_{1-3}$ alkanamido, may be prepared by the method described in Bender et al., U.S. Pat. No. 4,175,127, starting from the pyridine carboxyaldehyde cyanohydrin benzoate and the corresponding substituted benzaldehyde. Using this method with 3,4-methylenedioxybenzaldehyde and 4-pyridine carboxyaldehyde cyanohydrin benzoate afforded a mixture of 5/6-(4-pyridyl)-6/5-(3,4-methylenedioxypheny)-2,3-dihydroimidazo[2,1-b]thiazole isomers which were separated by chromatography on silica (methanol-methylene chloride, 2:98). The 6-pyridyl isomer eluted first, and was recrystallized from methanol to give the 6-(4-pyridyl) product, mp 213.5°-214.5° C. Analyzed for $C_{17}H_{13}N_3O_2S$; Calcd: C, 63.14; H, 4.05; N, 12.99; Found: C, 63.12; H, 4.10; N, 12.91. The 5-(4-pyridyl) product eluted next, and was also recrystallized from methanol, mp 177.5°-178.5° C. Analyzed for $C_{17}H_{13}N_3O_2S$; Calcd: C, 63.14; H, 4.05; N, 12.99; Found: C, 63.24; H, 4.20; N, 12.90.

EXAMPLE 7

5-(4-pyridyl)-6-(4-acetamidophenyl)-2,3-dihydroimidazo (2,1-b)thiazole and
6-(4-pyridyl)-5-(4-acetamidophenyl)-2,3-dihydroimidazo[2,1-b]thiazole Formula (I) compounds Employing the procedure of Example 6, and using 4-acetamidobenzaldehyde and 4-pyridine carboxaldehyde cyanohydrin benzoate as the starting materials, afforded a mixture of 5/6-(4-pyridyl)-6/5-(4-acetamidophenyl)-2,3-dihydroimidazo[2,1-b]thiazole isomers which were separated by chromatography on silica (methanol-methylene chloride, 2:98). The 5-(4-pyridyl) product eluted before the 6-(4-pyridyl) product.

EXAMPLE 8

5-(4-pyridyl)-6-(4-(pyrrolidin-1-yl)phenyl)-2,3-dihydroimida zo[2,1-b]thiazole Formula (I) compound a)
6-(4-pyrrolidin-1-yl)-phenyl)-2,3-dihydroimidazo[2,1-b]thiazole (Formula (III) compound)

To 250 ml of KOH dried pyridine was added 50 g (0.37 mole) of p-aminoacetophenone and 39.6 g of acetic anhydride. After one and a half hours of stirring at room temperature, the solution had become a thick suspension of a white solid. Filtration and drying gave 44 g of p-acetamidoacetophenone. This solid (44 g, 0.25 mole) was then suspended in 500 ml methylene chloride and treated with 44 g Br$_2$ (0.275 mole). The reaction was allowed to proceed overnight whereupon it was stripped and dried under high vacuum, then suspended in 200 ml absolute EtOH and treated with 60 g 2-amino-2-thiazoline (0.59 mole). The reaction was stirred for 2 days then stripped, taken up in water and extracted with methylene chloride. The organic phase was washed with water, brine and was dried with sodium sulfate. Flash column chromatography with 2% MeOH/98% CH$_2$Cl$_2$ gave 10.2 g (0.039 mole) of the Formula (III) compound, 6-acetamidophenyl-2,3-dihydroimidazo[2,1-b]thiazole.

The amide described above (10.2 g, 0.039 mole) was refluxed in 200 ml of 6N HCl for one hour, cooled, neutralized and extracted with methylene chloride. The organic layer was washed with brine, dried over sodium sulfate and evaporated to give 6.8 g of the Formula (III) compound 6-aminophenyl-2,3-dihydroimidazo[2,1-b]thiazole.

To 6.8 g (0.034 mole) of the amine described above in 150 ml of dry DMF was added 8.4 g (0.039 mole) 1,4-dibromobutane and 15.5 g K$_2$CO$_3$ (0.112 mole). The reaction was stirred at room temperature overnight, the DMF removed under high vacuum and the residue flash chromatographed on silica with 3% MeOH/97% CH$_2$Cl$_2$ to give (after recrystallization from MeOH) 0.88 g of the title Formula (III) compound, m.p. 218°–220° C. (dec.). Analyzed for C$_{15}$H$_{17}$N$_3$S, Calculated, C: 66:39, H: 6.31, N: 15.48; Found, C: 66.30, H: 6.32, N: 15.27.

b) 5-(4-pyridyl)-6-(4-(pyrrolidin-1-yl)-phenyl)-2,3-dihydroimidazo[2,1-b]thiazole (Formula (I) compound)

The procedure of Lantos et al., ibid, can be utilized to add a 4-pyridyl substituent at C-5 to either the tertiary amide, N-(C$_{1-3}$ alkyl)-alkanamidophenyl-2,3-dihydroimidazo[2,1-b]thiazole, or the tertiary amine, 6-(4-pyrrolidin-1-yl)phenyl-2,3-dihydroimidazo[2,1-b]thiazole. 5-(4-pyridyl)-6-(4-N-pyrrolidinophenyl)-2,3-dihydroimidazo[2,1-b]thiazole was prepared by this route and isolated by chromatography twice on silica (1. methanol-methylene chloride, 1.5:98.5, 2. ethyl acetate) to afford a glass. Analyzed for C$_{20}$H$_{20}$N$_4$S.O.875-H$_2$O; Calcd.: C, 65.95; H, 6.01; N, 15.38; Found: C, 65.98; H, 5.77; N, 15.16.

EXAMPLE 9

5-(4-pyridyl)-6-(4-fluorophenyl)-2,3-dihydroimidazo[2,1-b]thiazole-S-dioxide Formula (I) compound Compounds of Formula (I) where X is S(O)$_n$ and n is 1 or 2 are prepared by oxidation with one or two equivalents of an organic peracid as described in Bender et al., U.S. Pat. No. 4,263,311 and Bender et al., U.S. Pat. No. 4,175,127. Compounds of Formula (I) where at least one of R and R$^1$ is pyridyl, X is S(O)$_n$ and n=2 are preferably prepared by oxidation of 1 equivalent of an acid salt of X=S(O)$_n$, n is 1, with $\frac{2}{3}$ equivalent KMnO$_4$ aqueous in solution according to the method of Chatterway et al., J. Chem. Soc., 1352 (1930). Using this procedure, 5-(4-pyridyl)-6-(4-fluorophenyl)-2,3-dihydroimidazo[2,1-b]thiazole-S-oxide, prepared as described in Bender et al., U.S. Pat. No. 4,175,127, was cleanly oxidized to give the cyclic sulfone, after recrystallization from methanol, mp 250 dec. (Rf 0.73, silica, methanol-methylene chloride, 5:95). Analyzed for C$_{16}$H$_{12}$FN$_3$SO$_2$; Calcd.: C, 58.35; H, 3.67; N, 12.76; Found: C, 58.69; H, 3.86; N, 12.79.

EXAMPLE 10

5,6-bis(4-cyanophenyl)-2,3-dihydroimidazo[2,1-b]thiazole Formula (I) compound a) 2-Oxo-1,2-di(4-cyanophenyl)ethane To a solution of 25 g of p-cyanobenzaldehyde in 50 ml of ethanol was added 5 g of potassium cyanide in 10 ml of water. The mixture was heated at reflux for 1 hr, cooled, and the crystalline product was filtered and washed with cold ethanol. Recrystallization from acetic acid afforded 4.7 g of the part (a) title compound, mp. 209°–215° C.

b) 1-Bromo-2-oxo-1,2-di(4-cyanophenyl)ethane

A mixture of 3.8 g of 2-oxo-1,2-di(4-cyanophenyl) ethane, prepared as described above in part (a), and 7.2 g of cuprous bromide in 500 ml of ethylacetate and 500 ml of chloroform was refluxed for 3½ hours. The mixture was cooled, filtered through celite and the filtrate was evaporated to dryness. The residue was redissolved in ethyl acetate, washed with water, dried over magnesium sulfate and evaporated to dryness. The residue was titrated with ether to afford a crystalline product which was recrystallized from methanol-ester to afford the part (b) title compound, 3.9 g, mp. 167°–170°.

c) 5,6-bis(4-cyanophenyl)-2,3-dihydroimidazo[2,1-b]thiazole (Formula (I) compound)

A mixture of 3.8 g of 1-bromo-2-oxo-1,2-di(4-cyanophenyl)ethane, prepared as described above in part (b) and 3.8 g of 2-aminothiazoline in 70 ml of DMF was stirred at room temperature for 18 hours. The reaction mixture was diluted with cold water, and the precipitated product was filtered and dried in vacuum. The material was suspended in 200 ml of toluene, 125 mg of p-toluenesulfonic acid was added, and the mixture was refluxed for 2 hours with removal of water. After cooling, the crude product was filtered and recrystallized twice from acetic acid to afford the part (c) title compound, 1.3 g, m.p. 255°–260°; Analysis: C$_{19}$H$_{12}$N$_4$S.0.5AcO; Theory; C 67.03%, H 3.91%, N 15.64%; found C: 67.03% H: 3.96%, N: 15.04%.

EXAMPLE 11

6-(4-(1-Propylamino)phenyl)-5-(4-pyridyl)-2,3-dihydroimidazo[2,1-b]thiazole Formula (I) compound a) 6-(4-N-propylacetamido)phenyl-2,3-dihydroimidazo[2,1-b]thiazole (Formula (III) compound)

6-acetamidophenyl-2,3-dihydroimidazo[2,1-b]thiazole (1.0 g, 0.0038 mole), prepared as described in Example 8, was suspended in 25 ml dry DMF, and NaH (50% in oil, 0.21 g, 0.0046 mole) was added. The suspension slowly dissolved and after stirring at room temperature for 30 min., n-propylbromide (0.522 g, 0.0042 mole) was added to the reaction. The reaction was heated to 80° C. for one hour whereupon the DMF was removed under reduced pressure. The residue was then flash chromatographed (5% MeOH/95% CH$_2$Cl$_2$) to give 0.6 g of 6-(4-(N-propylacetamido)phenyl)-2,3-dihydro-imidazo[2,1-b]thiazole (Formula (III) compound) (TLC: R$_f$=0.31 2.5% MeOH/97.5% CH$_2$Cl$_2$).

b)
6-(4-(1-propylamino)phenyl)-5-(4-pyridyl)-2,3-dihydroimidazo[2,1-b]thiazole (Formula (I) compound)

The N-propylacetamido Formula (III) compound (0.60 g, 0.002 mole), prepared as described above in part a, was then suspended in $CH_2Cl_2$ (10 ml) and dry pyridine (0.47 ml, 0.006 mole) was added. The suspension was heated to aid in dissolving the solid, then cooled to ice-bath temperature. Ethyl chloroformate (0.72 ml, 0.648 g, 0.006 mole) in 2 ml $CH_2Cl_2$ was added dropwise to this mixture over a one hour period. The solution was stirred at room temperature for one hour and then heated at reflux for 10 min. The reaction was then cooled to 10° C. and an additional equivalent of pyridine (161 μl) and ethyl chloroformate (240 μl) was added. After heating at reflux for 10 min., the reaction was left to stir at room temperature overnight. The reaction was then washed with water (3×100 ml) and the organic layer stripped then decalin (5 ml) and sulfur (0.063 g, 0.002 mole) were added and the mixture was heated to 170° C. This temperature was maintained for one hour. The reaction was then diluted with $CH_2Cl_2$ and extracted with a 12% HCl solution. The acidic layer was basified with solid $K_2CO_3$ and then extracted with $CH_2Cl_2$. After treating with brine and $MgSO_4$, the $CH_2Cl_2$ was removed, and the residue was flash chromatographed (0.10% MeOH/100–90% $CH_2Cl_2$) to give 0.2 g of a (Formula (I) compound), 6-4-(N-propylacetamido)phenyl)-5-(4-pyridyl)-2,3-dihydroimidazo[2,1-b]thiazole (TLC: $R_f=0.22$ 5% MeOH/95% $CH_2Cl_2$.

The N-propylacetamido Formula (IB) compound (0.10 g, 0.26 mmole) was refluxed in 10 ml of 6N HCl for one hour, cooled, neutralized and extracted with methylene chloride. The organic layer was washed with brine, dried over sodium sulfate and evaporated to give 0.082 g of (6-(4-(N-propylamino)-phenyl)-5-(4-pyridyl)2,3-dihydro-imidazo[2,1-b]thiazole, (Formula (I) compound), as a glassy material (TLC: $R_f=0.35$ 8% MeOH/92% $CH_2Cl_2$, MS indicates presence of title compound, $(M+H)^+$ at 337).

EXAMPLE 12

5,6-Bis(4-pyridyl)-2,3-dihydroimidazo(2,1-b) thiazole Formula (I) compound 10 g (0.10 mole) of 4-pyridine carboxaldehyde was slowly added to a solution of 7.6 g (0.1 mole) of thiourea and 2.0 g (0.03 mole) in 50 ml water at 0° C. The solution was stirred at 0° C. for one hour, and then at ambient temperature overnight. A yellow precipitate of 4-pyridoin formed, which was filtered, dried and used without further purification.

A mixture of 1.1 g (5.4 mmoles) of the 4-pyridoin, prepared as described above, and 0.7 g (9.2 mmoles) of the thiourea was heated in 20 ml of dimethylacetamide at reflux for 6 hours. 4,5-Bis-(4-pyridyl)-2-mercaptoimidazole, a compound of Formula (IX), precipitated after dilution with water.

A solution of 2.90 g (11.5 mmoles) of the 2-mercaptoimidazole described above in 50 ml of DMF was treated with 1.64 g (11.5 mmoles) of 1-bromo-2-chloroethane, stirred at 100° C. for 1 hour. After treatment with a second 1.64 g of the dihaloethane, the reaction mixture was heated at 120° C. for an additional hour and then cooled. 4.2 g (30.4 mmoles) of powdered potassium carbonate was added and the mixture heated to reflux for one hour. The reaction mixture was concentrated in vacuo to 40 ml, diluted with cold water, and extracted into $CH_2Cl_2$. The organic phase was dried over sodium carbonate and concentrated in vacuo. The residue was column chromatographed on alumina and eluted with $CHCl_3$. Evaporation of the solvent gave an oil which crystallized on trituration with ether to afford the title Formula (I) compound, mp 219°–222° C. Analyzed for $C_{15}H_{12}N_4S$, Calculated, C: 64.26, H: 4.31, N: 19.98; Found C: 63.81, H: 4.57, N: 19.87.

UTILITY EXAMPLES

In the following Examples where mice were used, they were male Balb/c mice (20–28 g), and where rats were used, they were male Lewis rats (180–210 g). All mice and rats were obtained from Charles River Breeding Laboratories, Kingston, N.Y. Within a single experiment, mice and rats were sex and age matched.

In the following examples, reagents used were employed as follows:

Auranofin, phenidone, indomethacin, naproxen, and ibuprofen were each used as the free base. The compounds of Formula (I) were used either as the free base or in the appropriate salt form. Levamisole was used as the hydrochloride salt. The compounds were homogenized in 0.5% tragacanth. Compounds were administered by gavage at the indicated dose in a final volume of 10 ml/kg. Nordihydroguaiaretic acid (NDGA) was solubilized in dimethylacetamide and diluted with olive oil for subcutaneous administration.

For in vitro experiments, compounds were dissolved at appropriate concentrations in ethanol or DMSO (dimethylsulfoxide) (final concentration $\leq 1.0\%$) and then diluted to final concentrations using the buffers indicated in the text.

I. METHODS

Mouse Carrageenan Peritonitis

Mice were pretreated with either the test compound or vehicle one hour before the intraperitoneal injection of a 1.0% carrageenan suspension in saline (0.2 ml/mouse). Mice were sacrificed by cervical dislocation two hours after injection, and 3.0 ml of phosphate buffered saline, without $Ca^{++}$ or $Mg^{++}$, was injected into the peritoneum. Following massage, a 2.0 ml aliquot of the lavage fluid was removed, and the total cell count determined on a Coulter counter and differential cell count determined by microscopic examination of Giesma-stained slides.

Arachidonic Acid-Induced Mouse Ear Inflammation

Arachidonic acid in acetone (20 mg/20 μl) was applied to the inner surface of the left ear. The thickness of both ears was then measured with a dial micrometer one hour after treatment, and the data were expressed as the change in thickness ($10^{-3}$ cm) between treated and untreated ears.

Test compounds were given orally in 0.5% tragacanth at the times indicated in the text prior to the topical application of arachidonic acid.

Parenteral administration of compound was accomplished by subcutaneous injection of solution as indicated.

Arachidonic Acid-Induced Rat Paw Swelling

After determining pretreatment paw volumes by plethysmography by the method of Webb and Griswold, *J. Pharmacol. Methods*, 12, 149–153 (1984), rats were given test compound or vehicle one hour prior to the subplantar injection of 0.1 ml of 1 mg/ml arachidonic acid. Paw volumes were then remeasured and compared to pretreatment values and the increase in paw volume was expressed as mean values ± S.D.

Carrageenan and Arachidonic Acid-Induced Air Pouch Inflammation

Rats were shaved on the dorsal flank, and then injected subcutaneously one day later with 20 ml of air to form a defined pouch, by the method of Sedgwick et al., *J. Pathology*, 141, 483–495 (1983). The air pouch was reinflated as necessary over the next 6 days. To assay anti-inflammatory activity, animals were treated orally with test compound or vehicle (10 ml/kg) one hour before injection of 2.0 ml of a 2.0% carrageenan suspension containing 200 μ/ml penicillin and 100 g/ml streptomycin into the air pouch. In other experiments, 5 ml of 0.1% arachidonic acid in 0.2M bicarbonate buffer was injected two hours after drug treatment. Animals were sacrificed using $CO_2$ three hours after instillation of irritant. The exudate was then aspirated from the pouch and neutrophil count and differential cell count were measured.

$PGE_2$ Production by Peritoneal Macrophages

Mice were injected intraperitoneally with 350 μg *Corynebacterium parvum* and the peritoneal exudate cell population was harvested 12–14 days later by peritoneal lavage with cold phosphate-buffered saline, and resuspended in Eagles minimal essential medium supplemented with 5% fetal calf serum. The recovered cells, representing 95% macrophages as determined by morphology, phagocytic capacity and reactivity with a macrophage-specific monoclonal antibody [Koestler et al., *Proc. Natl. Acad. Sci., USA*, 81, 4504 (1984)], were placed in wells of 24-well microtiter plate ($10^6$ cells/900 μl) and allowed to adhere for 1 hour at 37° C. Test compounds were added (100 μl) to bring the final volume to 1.0 ml. Lipopolysaccharide (5 μg/ml) was then added to stimulate $PGE_2$ synthesis. After incubation at 37° C. for 2 hours, cell-free supernatants were harvested, placed in polypropylene tubes and frozen at −20° C. until assayed for their $PGE_2$ content using a commercial radioimmunoassay kit.

Assay of 5-Lipoxygenase and Cyclooxygenase Activities

The activities of these enzymes in extracts of RBL-1 cells were assayed using the method of Jakschik and Lee, *Nature*, 287, 51–52 (1980). RBL-1 cells were obtained from the American Type Culture Collection (#CRL 1378) and were grown at 37° C. (5% $CO_2$ in air) in spinner culture in MEM supplemented with 10% heat inactivated fetal calf serum. Harvested cells were washed with 50 mM sodium phosphate buffer, pH 7.0, containing 1 mM EDTA and 0.1% gelatin, resuspended in fresh buffer ($5 \times 10^7$ cells/ml) and disrupted by nitrogen cavitation using the Parr bomb at 750 psi for 10 min. The broken cell extract was then centrifuged at $10,000 \times$ g for 20 minutes (min) and the supernatant centrifuged at 100,000 xIg for 60 min. Aliquots (0.25 mls) of the supernatant were preincubated with or without drugs for 10 min, after which 10 μl $CaCl_2$ (50 mM) was added and the reaction was initiated with 2.5 μl of 2.5 mM arachidonic acid-1-$^{14}$C (final concentration was 25 μM; specific activity 20,000 dpm/nmole). After incubation for 3 min at 37° C., the reaction was terminated by addition of 2 volumes (0.5 ml) ice cold acetone and the sample was allowed to deproteinize on ice for 10 min prior to centrifugation at $1,000 \times$ g for 10 min. The deproteinized supernatant was adjusted to pH 3.5 with 2N formic acid and extracted with 2 volumes of ice cold ethyl acetate. The extracted samples were dried under argon, redissolved in ethyl acetate and applied to Whatman LK5D thin layer chromatography (TLC) plates which were developed using the A-9 solvent system [organic phase of ethyl acetate: 2,2,5-trimethylpentane:acetic acid: water (110:50:20:10)] described by Hamberg and Samuelsson, *J. Biol. Chem.*, 241, 257–263 (1966). Arachidonic acid, 5-HETE, $LTB_4$ and $PGD_2$ were quantified with a Berthold LB 2832 autoscanner.

The 5-lipoxygenase and $LTA_4$ synthetase activities were further studied under the following conditions. An additional centrifugation of the RBL-1 supernatant was run at $100,000 \times$ g for 60 min, to remove the particulate cyclooxygenase activity. Sample incubation was done under conditions similar to those described above, i.e., 2 mM $CaCl_2$ and 25M arachidonic acid-1-$^{14}$C, however, with an incubation time of 5 min at 5° C. Under these conditions, only the 5-lipoxygenase pathway metabolites were detectable. The 5-HETE and di-HETEs were formed at a linear rate, and substantial amounts of the arachidonic acid-1-$^{14}$C substrate were utilized.

Drug-induced effects on enzyme activities are described as the concentration of drug causing a 50% inhibition of metabolite synthesis ($IC_{50}$).

Ex Vivo Production of $LTB_4$ from Peritoneal Exudate Cells

Carrageenan-induced peritoneal exudate cells from normal or drug-treated mice were washed and suspended in 2.2 ml of phosphate buffered saline. Aliquots of $1-1.5 \times 10^7$ cells were suspended in 15 ml centrifuge tubes containing 5 ml of phosphate buffer (1.2 mM $Ca^{++}$). After incubation at room temperature for 30 minutes, cells were treated with the calcium ionophore A23187 (10 μM) for 5 minutes. The cell preparation was centrifuged at 1500 rpm for 10 min and the supernatant was extracted using a C-18 silica column. $LTB_4$ was separated by isocratic reverse phase high performance liquid chromatography using an Altex C-18 5 μM column attached to a Beckman Series 112 pump and a Beckman 254 detector set at 280 nm/0.01 AUFS. A tetrahydrofuran, methanol, water, acetic acid (25:30:45: 0.1) solvent system, adjusted to pH 5.5 with ammonium hydroxide, was used at a flow rate of 0.7 ml/min. Cell derived $LTB_4$ was quantified utilizing standard curves constructed with known amounts of synthetic $LTB_4$.

Experimental Allergic Encephalomyelitis Induced in Female Lewis Rats

The effect of Compound 1 and indomethacin on hindleg paralysis in experimental allergic encephalomyelitis induced in female Lewis rats was evaluated according to the following protocol. EAE is induced in Female (Charles River) Lewis rats by a single intradermal injection of 0.1 ml of an encephalitogenic emulsion consisting of equal parts of a 50% w/v homogenate of guinea pig spinal cord and mid-brain in 0.5% aqueous phenol and Freund's complete adjuvant (4 mg/ml killed, dried *M. butyricum*) into a hindpaw (left) footpad. Within 9–11 days, the animals exhibit tail limpness, hindleg weakness, and decrease in body weight. By day 16, the animals develop complete hindleg paralysis and exhibit a further decrease in body weight. Any animal which becomes paralyzed during the course of the experiment is considered to have developed EAE whether or not the paralysis is permanent. Test compounds are administered daily beginning on the day of injection, for 19 days, exclusive of days 5, 6 12 and 13. Drug activity is determined by comparing the indicidence of EAE (paralysis) of the treated group with a control (vehicle) group. The level of significant difference between the treated groups and control groups is determined by a Chi-square test using a 2×2 contingency table. Body weight changes from day 0 are also statistically compared to the control group using a Student "t" test.

$LTC_4$ Production by Human Monocytes

The compounds of Formula (I) were evaluated for their ability to inhibit the production of $LTC_4$ by human monocytes according to the following assay. Human monocytes were prepared from whole blood supplied by the American Red Cross. The blood was fractinated by a two-step procedure employing sedimentation on Ficoll followed by sedimentation on Percoll. The mononuclear cell fraction recovered was composed of 80-90% monocytes with the remainder of the cells being predominantly lymphocytes. The monocytes were plated at $1 \times 10^6$ cells per well in a costar 24 well tissue culture plate and allowed to adhere for 1 hour at 37° C. Non-adherent cells were removed by washing. The cells were stimulated with 1 µM A23187 calcium ionophore for 3 hours at 37° C. to induce $LTC_4$ production. When drugs were evaluated, they were added to the cells 30 minutes prior to the A23187. Supernatants were collected, clairified by centrifugation and stored frozed at $-20°$ C. until assay. The $LTC_4$ content was determined by using a New England Nuclear Leukotriene C-4 ($^3$H) RIA Kit as per instructions.

II. RESULTS

The Effects of Compound 1 on Leukocyte Infiltration into Inflammatory Lesions

The effect of Compound 1 on the infiltration of cells into inflammatory lesions was examined in several assay systems. As shown in Table 1, the infiltration of polymorphonuclear leukocytes induced by intraperitoneal injection of carrageenan in mice is reduced dramatically by oral administration of Compound 1. The inhibition is dose-related, with an $ED_{50}$ of 43.9 mg/kg, p.o. Also, the leukotriene synthesis inhibitors phenidone (Table 1), NDGA and dexamethasone (Table 2) were effective in PMN infiltration in this peritonitis model. In contrast, the cyclooxygenase inhibitors indomethacin (10 mg/kg, p.o.) and naproxen (100 mg/kg, p.o.), the organo-gold compound auranofin (2 mg Au/kg, p.o.) and levamisole (100 mg/kg, p.o.) did not impair inflammatory cell infiltration in this assay system despite the use of near maximally tolerated doses (Table 3). Compound 1 also produced significant inhibition of polymorphonuclear leukocyte infiltration into rat air pouch inflammatory lesions induced by carrageenan (Table 4). The reduction in PMN infiltration was accompanied by a relative increase in mononuclear cell counts. A reduction in the PMN count and the PMN:mononuclear cell ratio was also produced by phenidone (100 mg/kg, p.o.) and a high dose of indomethacin (5 mg/kg, p.o.). Unlike the mouse carrageenan model, this assay system was sensitive to the anti-inflammatory activity of indomethacin.

The Effect of Compound 1 on Arachidonic Acid-induced Inflammation

In order to help define the anti-inflammatory properties of Compound 1, inflammatory lesions were induced using arachidonic acid. As shown in Table 5, Compound 1 and phenidone significantly reduced PMN and mononuclear cell infiltration into arachidonic acid-induced inflammation in the rat air pouch but indomethacin had no significant effect on cell infiltration. Further elucidation of the anti-inflammatory activity of Compound 1 was achieved in models of arachidonic acid-induced edema in mice and rats. The mouse ear edematous response to arachidonic acid has been shown to be sensitive to agents that inhibit both lipoxygenase and cyclooxygenase-generated mediators or that selectively inhibit lipoxygenase, but not cyclooxygenase, enzyme activity [See, Young et al., *J. Invest. Dermatol.*, 82, 367–371 (1984)]. The inflammatory response induced in rat paws by arachidonic acid injection was inhibited significantly by both Compound 1 and phenidone, but not by indomethacin (Table 6). Similarly, Compound 1 produced marked inhibition of the edematous response normally seen 1 hour after the application of 2 mg of arachidonic acid to the ear ($ED_{50}$ of 19.5 mg/kg, p.o.). The anti-inflammatory activity of Compound 1 in this assay is greater than for phenidone ($ED_{50}=44.0$ mg/kg, p.o.) and for dexamethasone which was only moderately effective. The cyclooxygenase inhibitors, indomethacin (10 mg/kg, p.o.), ibuprofen (250 mg/kg, p.o.) and naproxen (100 mg/kg, p.o.) did not exhibit detectable anti-inflammatory activity in this assay, despite use at near maximally tolerated doses (Table 7). Table 7A represents the results of testing other compounds of Formula (I) in the arachidonic acid-induced ear swelling assay. Such results indicate that the compounds of Formula (I) exhibit antiinflammatory activity in an assay in which selective cyclooxygenase inhibitors do not exhibit such activity.

Collectively, these findings indicate that Compound 1 is a potent inhibitor of both the cellular and edematous responses of inflammation in rats and mice. These inflammatory responses were also inhibited by agents that inhibit lipoxygenase activity but not by selective cyclooxygenase inhibitors.

The Effect of Compound 1 on Arachidonic Acid Metabolism

The generation of the 5-lipoxygenase product, $LTB_4$, and the generation of the cyclooxygenase product, $PGD_2$, by RBL-1 cell extracts can be distinguished as shown by the inhibition of $PGD_2$ production by indomethacin ($IC_{50}=2.5$ µM) and the inhibition of 5-HETE synthesis by phenidone ($IC_{50}=10$ µM) (Table 8). The generation of both enzyme products was inhibited, however, by Compound 1, with $IC_{50}$ values of 75 µM and 100 µM for 5-HETE and $PGD_2$, respectively. The effect of other compounds of Formula (I) on the inhibition of 5-HETE is presented in Table 8A which indicates that compounds of Formula (I) are inhibitors of the 5-lipoxygenase pathway as evidenced by their ability to inhibit 5-HETE a 5-lipoxygenase pathway product.

Additional experiments using a soluble extract preparation of RBL-1 cells containing only lipoxygenase activity ($LTB_4$ production by RB1-cells) confirmed the inhibitory effects of Compound 1 on eicosanoid formation ($IC_{50} = 7.5$ μM) (Table 9). Indomethacin at concentrations up to $10^{-4}$M was inactive.

Table 9A represents the testing of compounds of Formula (I) for their ability to inhibit 5-lipoxygenase activity. The results presented in Table 9A indicate that the compounds of Formula (I) possess 5-lipoxygenase pathway inhibiting activity as evidenced by their ability to inhibit $LTB_4$, a 5-lipoxygenase pathway product.

The production of $PGE_2$ by inflammatory macrophages is inhibited by Compound 1 (Table 10). The $IC_{50}$ value of 0.7 μM in this assay is comparable to those exhibited by the non-steroidal anti-inflammatory agents, ibuprofen and naproxen ($IC_{50} = 0.5$ μM and 1.8 μM, respectively) and higher than that of indomethacin ($IC_{50} = 0.04$ μM). Phenidone proved much less active in inhibiting $PGE_2$ production by inflammatory macrophages ($IC_{50} = 28$ μM).

To establish whether Compound 1 at doses shown to be effective in inhibiting inflammatory responses in vivo inhibited $LTB_4$ synthesis by inflammatory cells, the ability of peritoneal exudate cells obtained from drug-treated animals to produce $LTB_4$ in vitro was determined. Impairment of $LTB_4$ production was observed in peritoneal exudate cells obtained from animals treated with Compound 1 (100 mg/kg, p.o.), as compared to those from vehicle-treated controls. Under the same experimental conditions, phenidone exhibited a weaker but inhibition of $LTB_4$ synthesis, whereas naproxen was inactive (Table 11).

The Effect of Compound 1 on Hindleg Paralysis in Experimental Allergic Encephalomyelitis Induced in Female Lewis Rats As shown in Table 12, Compound 1, but not indomethacin, was efficacious in inhibiting experimental allergic encephalomyelitis (EAE) in rats.

$LTC_4$ Inhibition Assay

As shown in Table 13, compounds of Formula (I) were efficacious in inhibiting $LTC_4$ production by human monocytes. These data confirm the ability of compounds of Formula (I) to inhibit the 5-lipoxygenase pathway, as evidenced by their ability to inhibit $LTC_4$, a 5-lipoxygenase pathway product.

As seen in Table 7A not all compounds of Formula (I) significantly inhibited arachidonic acid-induced ear swelling, but such non-significant inhibitors of ear swelling did significantly inhibit the production of 5-HETE by RBL-1 high speed supernatant (Table 8A), the production of $LTB_4$ by RBL-1 high speed supernatant (Table 9A) and/or the production of $LTC_4$ by human monocytes (Table 13) indicating that such compounds are inhibitors of the 5-lipoxygenase pathway.

TABLE 1

The Effect of Compound 1 and Phenidone on the Infiltration of Polymorphonuclear Leukocytes into Sites of Carrageenan-Induced Inflammation

| Treatment[a] | PMN × $10^{-5}$/ml (mean ± S.D.) | % Change |
|---|---|---|
| Vehicle | 10.90 ± 0.89 | — |
| Compound 1 | | |
| 100 mg/kg, p.o. | 2.48 ± 0.98 | −77[b] |
| 50 mg/kg, p.o. | 4.84 ± 3.01 | −56[c] |
| 25 mg/kg, p.o. | 7.92 ± 4.15 | −27[e] |
| Phenidone | | |
| 200 mg/kg, p.o. | 0.66 ± 0.53 | −94[b] |
| 100 mg/kg, p.o. | 6.97 ± 3.81 | −36[d] |

TABLE 1-continued

The Effect of Compound 1 and Phenidone on the Infiltration of Polymorphonuclear Leukocytes into Sites of Carrageenan-Induced Inflammation

| Treatment[a] | PMN × $10^{-5}$/ml (mean ± S.D.) | % Change |
|---|---|---|
| 50 mg/kg, p.o. | 5.30 ± 2.25 | −51[c] |

[a]Mice were pretreated with the compounds indicated one hour prior to the i.p. injection of carrageenan, and cellular infiltration was measured two hours later as described in the Methods. The data represent mean values (± S.D.) derived from measurements on five animals in each treatment group.
[b]Statistically significant: P < 0.001.
[c]Statistically significant: P < 0.01.
[d]Statistically significant: P < 0.05.
[e]Not Significant.

TABLE 2

The Effect of Dexamethasone and NDGA on the Infiltration of Polymorphonuclear Leukocytes into Sites of Carrageenan-Induced Inflammation

| Treatment[a] | PMN × $10^{-5}$/ml (mean ± S.D.) | % Change |
|---|---|---|
| Experiment 1 | | |
| Vehicle, p.o. | 19.8 ± 3.2 | — |
| Dexamethasone | | |
| 50 mg/kg, p.o. | 6.1 ± 1.5 | −69[b] |
| 25 mg/kg, p.o. | 8.8 ± 2.6 | −55[b] |
| 12.5 mg/kg, p.o. | 9.1 ± 2.0 | −54[b] |
| Experiment 2 | | |
| Vehicle, s.c. | 9.7 ± 3.1 | — |
| NDGA | 5.7 ± 2.1 | 41[c] |
| 50 mg/kg, s.c. | | |

[a]Mice were pretreated with the compounds indicated one hour prior to the i.p. injection of carrageenan, and cellular infiltration was measured two hours later as described in the Methods. The data represent mean values (± S.D.) derived from measurements on 5 animals in each treatment group.
[b]Statistically significant at a P < 0.001.
[c]Statistically significant at a P < 0.01.

TABLE 3

The Effect of Indomethacin, Naproxen, Levamisole and Auranofin on the Infiltration of Polymorphonuclear Leukocytes into Sites of Carrageenan-Induced Inflammation

| Treatment[a] | Dosage mg/kg. p.o. | PMN × $10^{-5}$/ml (Mean ± S.D.) | % Change |
|---|---|---|---|
| Indomethacin | 10 | 8.20 ± 2.65 | −12[b] |
| Naproxen | 100 | 10.28 ± 2.49 | −11[b] |
| Levamisole | 100 | 5.88 ± 2.70 | −37[b] |
| Auranofin | 2 (mg Au/kg) | 7.50 ± 1.57 | −6[b] |

[a]Experiments were conducted using the protocol described in Table 1. The results represent mean values (± S.D.) derived from measurements on 5 animals/group. Control values for these experiments ranged from 7.8 ± 2.59 to 11.49 ± 3.56 PMN × $10^{-5}$/ml.
[b]Not statistically significant.

TABLE 4

The Effect of Compound 1, Phenidone and Indomethacin on Carrageenan-Induced Cellular Infiltration into the Rat "Air Pouch."[a]

| Treatment | Exudate Volume (ml) | Cellular Infiltrate (Total × $10^{-6}$) | | PMN/MN Ratio |
|---|---|---|---|---|
| | | PMN[b] | MN[c] | |
| Control | 1.8 ± 0.8 | 6.3 ± 4.0 | 2.8 ± 0.7 | 2.21 ± 1.09 |
| Phenidone (100 mg/kg) | 1.5 ± 0.8 | 1.7 ± 0.6[d] | 3.5 ± 1.4 | 0.52 ± 0.13[d] |
| Compound 1 (100 mg/kg) | 1.0 ± 0.9 | 2.6 ± 1.3[d] | 5.5 ± 3.8[e] | 0.50 ± 0.14[d] |
| Indomethacin | 2.0 ± 0.5 | 2.8 ± 0.7[d] | 4.0 ± 0.8 | 0.69 ± 0.19[d] |

TABLE 4-continued

The Effect of Compound 1, Phenidone and Indomethacin on Carrageenan-Induced Cellular Infiltration into the Rat "Air Pouch."[a]

| Treatment | Exudate Volume (ml) | Cellular Infiltrate (Total × 10⁻⁶) | | PMN/MN Ratio |
|---|---|---|---|---|
| | | PMN[b] | MN[c] | |
| (5 mg/kg) | | | | |

[a]Cell infiltration was measured 3 hours after injection of carrageenan into a preformed air pouch as described in the Methods. The results represent mean values (± S.D.) derived from measurements on 8 animals.
[b]Polymorphonuclear leukocytes.
[c]Mononuclear leukocytes.
[d]Statistically significant at a P < 0.01.
[e]Statistically significant at a P < 0.05.

TABLE 5

The Effect of Compound 1, Phenidone and Indomethacin on Arachidonic Acid-Induced Cellular Infiltration into the Rat "Air Pouch."[a]

| Treatment | Exudate Volume (ml) | Cellular Infiltrate (Total × 10⁻⁶) | | PMN/MN Ratio |
|---|---|---|---|---|
| | | PMN[b] | MN[c] | |
| Control | 2.8 ± 0.7 | 4.4 ± 3.7 | 9.8 ± 4.7 | 0.65 ± 0.62 |
| Compound 1 (100 mg/kg) | 2.6 ± 0.8 | 1.2 ± 0.7[e] | 1.5 ± 1.1[d] | 1.20 ± 0.88 |
| Phenidone (100 mg/kg) | 2.8 ± 0.4 | 1.3 ± 0.8[e] | 2.2 ± 1.5[d] | 0.74 ± 0.39 |
| Indomethacin (5 mg/kg) | 2.5 ± 0.8 | 5.0 ± 3.8 | 7.0 ± 6.4 | 0.94 ± 0.83 |

[a]Cell infiltration was measured 3 hours after injection of arachidonic acid into a preformed air pouch as described in the Methods. The results represent mean values (± S.D.) derived from measurement of 6 to 8 animals.
[b]Polymorphonuclear leukocytes.
[c]Mononuclear leukocytes.
[d]Statistically significant at a P < 0.01.
[e]Statistically significant at a P < 0.05.

TABLE 6

The Effect of Compound 1, Phenidone and Indomethacin on Arachidonic Acid-Induced Rat Paw Edema.[a]

| Treatment | Change in Paw Volume (ml) (% Inhibition) |
|---|---|
| Control | 0.27 ± 0.05 |
| Compound 1 (100 mg/kg) | 0.06 ± 0.05[b] (78) |
| Phenidone (100 mg/kg) | 0.13 ± 0.05[b] (52) |
| Indomethacin (5 mg/kg) | 0.29 ± 0.06 (0) |

[a]Animals were treated with the indicated compounds one hour before subplantar injection of arachidonic acid. The results represent mean values (± S.D.) derived from measurements on 8 animals read at 2 hours post arachidonic acid injection.
[b]Statistically significant at a P < 0.01.

TABLE 7

The Effect of Compound 1, Phenidone and Selected Compounds on Arachidonic Acid-Induced Inflammation of the Mouse Ear.[a]

| Treatment | Dose (mg/kg, p.o.) | Increase in Ear Thickness at 1 Hour (× 10⁻³ cm) | % Change |
|---|---|---|---|
| Compound 1 | 50 | 10.0 ± 1.5 | −67[b] |
| Phenidone | 50 | 12.2 ± 1.6 | −57[b] |
| Dexamethasone | 25 | 18.2 ± 4.1 | −35[c] |
| Indomethacin | 10 | 24.4 ± 0.8 | −5 |
| Naproxen | 100 | 26.4 ± 2.6 | +3 |
| Ibuprofen | 250 | 30.8 ± 2.0 | +20[b] |

[a]Compounds were administered 15 minutes (dexamethasone was pretreated at 2 hrs) before application of arachidonic acid to the ear as described in the Methods. The results represent mean values (± S.D.) derived from measurements on 5 animals. Control values for these experiments ranged from 28.1 ± 0.8 to 30.0 ± 1.3.
[b]Statistically significant at a P < 0.001.
[c]Statistically significant at a P < 0.0005.

TABLE 7A

The Effect of Compounds of Formula I on Arachidonic Acid-Induced Ear Swelling

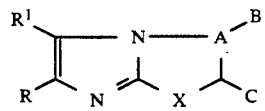

Formula (I)

| Compound Number | R¹ | R | X | A | n | % Inhibition[a,b] of Ear Swelling |
|---|---|---|---|---|---|---|
| 2 | 4-pyridyl | 4-(1-propylamino)phenyl | S(O)n | CH₂ | 0 | 23* |
| 3 | 4-(pyrrolidin-1-yl)phenyl | 4-(pyrrolidin-1-yl)phenyl | S(O)n | CH₂ | 0 | 44*** |
| 4 | 4-(piperidin-1-yl)phenyl | 4-(piperidin-1-yl)phenyl | S(O)n | CH₂ | 0 | 22* |
| 5 | 4-pyridyl | 3,4-(methylenedioxy)phenyl | S(O)n | CH₂ | 0 | NS |
| 6 | 4-fluorophenyl | 4-dimethylaminophenyl | S(O)n | CH₂ | 0 | 48*** |
| 7 | 3,4-(methylenedioxy)phenyl | 4-pyridyl | S(O)n | CH₂ | 0 | 62*** |
| 8 | 4-fluorophenyl | 4-fluorophenyl | CH₂ | CH₂ | — | 40***(p.o.) |
| 9 | 4-diethylaminophenyl | 4-diethylaminophenyl | S(O)n | CH₂ | 0 | 17* (p.o.) |
| 10 | 4-dimethylaminophenyl | 4-fluorophenyl | S(O)n | CH₂ | 0 | 7* |
| 11 | 4-pyridyl | 4-pyridyl | S(O)n | CH₂ | 0 | 29*** |
| 12 | 4-fluorophenyl | 4-pyridyl | S(O)n | CH₂ | 0 | 58*** |
| 13 | 4-cyanophenyl | 4-cyanophenyl | S(O)n | CH₂ | 0 | 50*** |
| 14 | 4-fluorophenyl | 4-methoxyphenyl | S(O)n | CH₂ | 0 | 64*** |
| 15 | 4-trifluoromethylphenyl | 4-trifluoromethylphenyl | S(O)n | CH₂ | 0 | NS (p.o.) |
| 16 | 3,4-methylenedioxyphenyl | 3,4-methylenedioxyphenyl | S(O)n | CH₂ | 0 | 32***(p.o.) |
| 17 | 4-ethylaminophenyl | 4-ethylaminophenyl | S(O)n | CH₂ | 0 | 38*** |
| 18 | 4-pyridyl | 4-methoxyphenyl | S(O)n | CH₂ | 0 | 40***(p.o.) |
| 19 | 4-fluorophenyl | 4-fluorophenyl | S(O)n | CH₂ | 0 | 34***(p.o.) |
| 20 | 4-methoxyphenyl | 4-methoxyphenyl | S(O)n | CH₂CH₂ | 0 | 47*** |
| 21 | 4-methoxyphenyl | 4-methoxyphenyl | S(O)n | CH₂ | — | NS (p.o.) |
| 22 | 4-methoxyphenyl | 4-methoxyphenyl | CH₂ | CH₂ | — | 15* |
| 23 | 2-pyridyl | 4-fluorophenyl | S(O)n | CH₂ | 0 | 65*** |
| 24 | 4-fluorophenyl | 2-pyridyl | S(O)n | CH₂ | 0 | 69*** |
| 25 | 4-pyridyl | 4-(pyrrolidin-1-yl)phenyl | S(O)n | CH₂ | 0 | 17* (p.o.) |
| 26 | 4-fluorophenyl | 4-fluorophenyl(hydrate) | S(O)n | CH₂ | 0 | NT |
| 27 | 4-fluoromethylphenyl | 4-trifluoromethylphenyl (hydrate) | S(O)n | CH₂ | 0 | NT |

TABLE 7A-continued

The Effect of Compounds of Formula I on Arachidonic Acid-Induced Ear Swelling

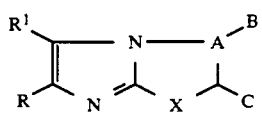

Formula (I)

| Compound Number | R¹ | R | X | A | n | % Inhibition[a,b] of Ear Swelling |
|---|---|---|---|---|---|---|
| 28 | 4-pyridyl | 4-fluorophenyl | S(O)n | CH$_2$ | 1 | 69*** |
| 29 | 4-pyridyl | 4-fluorophenyl | S(O)n | CH$_2$ | 2 | 67*** (p.o.) |
| 30 | 4-fluorophenyl | 4-fluorophenyl | S(O)n | CH$_2$ | 1 | NT |
| 31 | 4-fluorophenyl | 4-fluorophenyl | S(O)n | CH$_2$ | 2 | NT |
| 32 | 4-methylthiophenyl | 4-methylthiophenyl | S(O)n | CH$_2$ | 0 | NS (p.o.) |
| 33 | phenyl | phenyl | S(O)n | CH$_2$ | 0 | NT |
| 34 | 4-methylphenyl | 4-methylphenyl | S(O)n | CH$_2$ | 0 | NT |
| 35 | 4-(prop-2-ene-1-oxy)phenyl | 4-(prop-2-ene-1-oxy)phenyl | S(O)n | CH$_2$ | 0 | NT |
| 36 | 4-(2,2,2-trifluoroethoxy)phenyl | 4-(2,2,2-trifluoroethyoxy)phenyl | S(O)n | CH$_2$ | 0 | NT |
| 37 | 3,4,5-trimethoxyphenyl | 3,4,5-trimethoxyphenyl | S(O)n | CH$_2$ | 0 | NT |
| 38 | 4-pyridyl | 4-acetamidophenyl | S(O)n | CH$_2$ | 0 | NT |

[a] Screened at 50 mg/kg s.c. or i.p. unless indicated as oral dosing (p.o.).
[b] * = p .05,  = p .01, *p .001, NS = not siginificant, NT = not tested

TABLE 8

The Effect of Compound 1, Phenidone and Indomethacin on Cyclooxygenase and 5-Lipoxygenase Activities in RBL-1 Cells.[a]

| Treatment | IC$_{50}$ (mM) Cyclooxygenase | 5-Lipoxygenase |
|---|---|---|
| Compound 1 | 100 | 75 |
| Phenidone | Inactive @ 100 | 10 |
| Indomethacin | >2.5 | Inactive @ 30 |

[a] Enzyme activities were measured by the amount of PGD$_2$ and 5-HETE produced from $^{14}$C-labeled arachidonic acid incubated with the 10,000 × g supernatant of RBL-1 cells as described in the Methods.

TABLE 8A

The Effect of Compounds of Formula I on 5-HETE Production

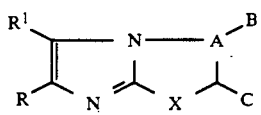

Formula (I)

| Compound Number | R¹ | R | X | A | n | 5-HETE[a,b] IC$_{50}$ (μM) |
|---|---|---|---|---|---|---|
| 2 | 4-pyridyl | 4-(1-propylamino)phenyl | S(O)n | CH$_2$ | 0 | 12 |
| 3 | 4-(pyrrolidin-1-yl)phenyl | 4-(pyrrolidin-1-yl)phenyl | S(O)n | CH$_2$ | 0 | .23 |
| 4 | 4-(piperidin-1-yl)phenyl | 4-(piperidin-1-yl)phenyl | S(O)n | CH$_2$ | 0 | 1.2 |
| 5 | 4-pyridyl | 3,4-(methylenedioxy)phenyl | S(O)n | CH$_2$ | 0 | 10 |
| 6 | 4-fluorophenyl | 4-dimethylaminophenyl | S(O)n | CH$_2$ | 0 | .80 |
| 7 | 3,4-(methylenedioxy)phenyl | 4-pyridyl | S(O)n | CH$_2$ | 0 | 10 |
| 8 | 4-fluorophenyl | 4-fluorophenyl | CH$_2$ | CH$_2$ | — | 12 |
| 9 | 4-diethylaminophenyl | 4-diethylaminophenyl | S(O)n | CH$_2$ | 0 | .35 |
| 10 | 4-dimethylaminophenyl | 4-fluorophenyl | S(O)n | CH$_2$ | 0 | 5 |
| 11 | 4-pyridyl | 4-pyridyl | S(O)n | CH$_2$ | 0 | 110 |
| 12 | 4-fluorophenyl | 4-pyridyl | S(O)n | CH$_2$ | 0 | 16 |
| 13 | 4-cyanophenyl | 4-cyanophenyl | S(O)n | CH$_2$ | 0 | 16 |
| 14 | 4-fluorophenyl | 4-methoxyphenyl | S(O)n | CH$_2$ | 0 | 2 |
| 15 | 4-trifluoromethylphenyl | 4-trifluoromethylphenyl | S(O)n | CH$_2$ | 0 | 10 |
| 16 | 3,4-methylenedioxyphenyl | 3,4-methylenedioxyphenyl | S(O)n | CH$_2$ | 0 | 3.8 |
| 17 | 4-ethylaminophenyl | 4-ethylaminophenyl | S(O)n | CH$_2$ | 0 | .10 |
| 18 | 4-pyridyl | 4-methoxyphenyl | S(O)n | CH$_2$ | 0 | 5.4 |
| 19 | 4-fluorophenyl | 4-fluorophenyl | S(O)n | CH$_2$ | 0 | 8.6 |
| 20 | 4-methoxyphenyl | 4-methoxyphenyl | S(O)n | CH$_2$CH$_2$ | 0 | 5.6 |
| 21 | 4-methoxyphenyl | 4-methoxyphenyl | S(O)n | CH$_2$ | 0 | 3.9 |
| 22 | 4-methoxyphenyl | 4-methoxyphenyl | CH$_2$ | CH$_2$ | 0 | 4.0 |
| 23 | 2-pyridyl | 4-fluorophenyl | S(O)n | CH$_2$ | 0 | 90 |
| 24 | 4-fluorophenyl | 2-pyridyl | S(O)n | CH$_2$ | 0 | 37 |
| 25 | 4-pyridyl | 4-(pyrrolidin-1-yl)phenyl | S(O)n | CH$_2$ | 0 | .5 |
| 26 | 4-fluorophenyl | 4-fluorophenyl(hydrate) | S(O)n | CH$_2$ | 0 | >10(C) |
| 27 | 4-trifluoromethylphenyl | 4-trifluoromethylphenyl (hydrate) | S(O)n | CH$_2$ | 0 | 28 |
| 28 | 4-pyridyl | 4-fluorophenyl | S(O)n | CH$_2$ | 1 | 1000 |

TABLE 8A-continued

The Effect of Compounds of Formula I on 5-HETE Production

Formula (I)

| Compound Number | $R^1$ | R | X | A | n | 5-HETE[a,b] $IC_{50}$ (μM) |
|---|---|---|---|---|---|---|
| 29 | 4-pyridyl | 4-fluorophenyl | S(O)n | $CH_2$ | 2 | 100 |
| 30 | 4-fluorophenyl | 4-fluorophenyl | S(O)n | $CH_2$ | 1 | 70 |
| 31 | 4-fluorophenyl | 4-fluorophenyl | S(O)n | $CH_2$ | 2 | 33 |
| 32 | 4-methylthiophenyl | 4-methylthiophenyl | S(O)n | $CH_2$ | 0 | >10(D) |
| 33 | phenyl | phenyl | S(O)n | $CH_2$ | 0 | NT |
| 34 | 4-methylphenyl | 4-methylphenyl | S(O)n | $CH_2$ | 0 | NT |
| 35 | 4-(prop-2-ene-1-oxy)phenyl | 4-(prop-2-ene-1-oxy)phenyl | S(O)n | $CH_2$ | 0 | NT |
| 36 | 4-(2,2,2-trifluoroethoxy)phenyl | 4-(2,2,2-trifluoroethoxy)phenyl | S(O)n | $CH_2$ | 0 | NT |
| 37 | 3,4,5-trimethoxyphenyl | 3,4,5-trimethoxyphenyl | S(O)n | $CH_2$ | 0 | NT |
| 38 | 4-pyridyl | 4-acetamidophenyl | S(O)n | $CH_2$ | 0 | 69 |

[a]$IC_{50}$ determined on 5-HETE reduction by RBL-1 high speed supernatant
[b]NT = not tested
(C) 46% inhibition at 10 μM
(D) 35-40% inhibition at 10 μM

TABLE 9

The Effect of Compound 1 on the Production of Di-HETE and 5-HETE by the High Speed Supernatant of RBL-1 Cells.[a]

| Treatment | Di-HETE (nM/ml) | % Control | 5-HETE (nM/ml) | % Control |
|---|---|---|---|---|
| Control | 1.94 ± 0.11 | — | 10.15 ± 0.65 | — |
| Compound 1 | | | | |
| 1 μM | 1.56 ± 0.06 | 19.7[b] | 8.86 ± 0.31 | 12.7[b] |
| 3.3 μM | 1.34 ± 0.12 | 30.9[b] | 7.63 ± 0.44 | 24.9[b] |
| 10 μM | 0.88 ± 0.21 | 54.8[b] | 5.57 ± 0.35 | 45.1[b] |
| 33 μM | 0.40 ± 0.08 | 79.6[b] | 3.36 ± 0.07 | 67.9[b] |
| 100 μM | 0.03 ± 0.04 | 98.3[b] | 1.08 ± 0.13 | 89.4[b] |

[a]Enzyme activities were measured by the production of 5-HETE and Di-HETE from $^{14}$C-labeled arachidonic acid incubated with a high speed supernatant of RBL-1 cells (see Methods for details). The results represent mean values (± S.D.) derived from measurements on 4 replicate analyses.
[b]Statistically significant from Control at a P < 0.01 or better.

TABLE 9A

The Effect of Compounds of Formula I on Lipoxygenase Activity (LTB₄ Production)

Formula (I)

| Compound Number | $R^1$ | R | A | X | n | 5-LO[a,b] $IC_{50}$(μM) |
|---|---|---|---|---|---|---|
| 2 | 4-pyridyl | 4-(1-propyl)aminophenyl | $CH_2$ | S(O)n | 0 | 7 |
| 3 | 4-(pyrrolidin-1-yl)phenyl | 4-(pyrrolidin-1-yl)phenyl | $CH_2$ | S(O)n | 0 | 0.1 |
| 4 | 4-(piperidin-1-yl)phenyl | 4-(piperidin-1-yl)phenyl | $CH_2$ | S(O)n | 0 | 0.6 |
| 5 | 4-pyridyl | 3,4-(methylenedioxy)phenyl | $CH_2$ | S(O)n | 0 | 10.0 |
| 6 | 4-fluorophenyl | 4-dimethylaminophenyl | $CH_2$ | S(O)n | 0 | 0.6 |
| 7 | 3,4-(methylenedioxy)phenyl | 4-pyridyl | $CH_2$ | S(O)n | 0 | 10.0 |
| 8 | 4-fluorophenyl | 4-fluorophenyl | $CH_2$ | S(O)n | | 8.0 |
| 9 | 4-diethylaminophenyl | 4-diethylaminophenyl | $CH_2$ | S(O)n | 0 | 0.16 |
| 10 | 4-dimethylaminophenyl | 4-fluorophenyl | $CH_2$ | S(O)n | 0 | 1.5 |
| 11 | 4-pyridyl | 4-pyridyl | $CH_2$ | S(O)n | 0 | 33.0 |
| 12 | 4-fluorophenyl | 4-pyridyl | $CH_2$ | S(O)n | 0 | 17.0 |
| 13 | 4-cyanophenyl | 4-cyanophenyl | $CH_2$ | S(O)n | 0 | 15.0 |
| 14 | 4-fluorophenyl | 4-methoxyphenyl | $CH_2$ | S(O)n | 0 | 0.6 |
| 15 | 4-trifluoromethylphenyl | 4-trifluoromethylphenyl | $CH_2$ | S(O)n | 0 | 10.0 |
| 16 | 3,4-methylenedioxyphenyl | 3,4-methylenedioxyphenyl | $CH_2$ | S(O)n | 0 | 1.5 |
| 17 | 4-ethylaminophenyl | 4-ethylaminophenyl | $CH_2$ | S(O)n | 0 | 0.1 |
| 18 | 4-pyridyl | 4-methoxyphenyl | $CH_2$ | S(O)n | 0 | 1.9 |
| 19 | 4-fluorophenyl | 4-fluorophenyl | $CH_2$ | S(O)n | 0 | 5.0 |
| 20 | 4-methoxyphenyl- | 4-methoxyphenyl | $CH_2CH_2$ | S(O)n | 0 | 5.6 |
| 21 | 4-methoxyphenyl | 4-methoxyphenyl | $CH_2$ | S(O)n | 0 | 2.8 |
| 22 | 4-methoxyphenyl | 4-methoxyphenyl | $CH_2$ | $CH_2$ | | NT |
| 23 | 2-pyridyl | 4-fluorophenyl | $CH_2$ | S(O)n | 0 | 42 |
| 24 | 4-fluorophenyl | 2-pyridyl | $CH_2$ | S(O)n | 0 | 20 |
| 25 | 4-pyridyl | 4-(pyrrolidin-1-yl)phenyl | $CH_2$ | S(O)n | 0 | 0.5 |
| 26 | 4-fluorophenyl | 4-fluorophenyl(hydrate) | $CH_2$ | S(O)n | 0 | >10 |
| 27 | 4-trifluoromethylphenyl | 4-trifluoromethylphenyl (hydrate) | $CH_2$ | S(O)n | 0 | NT |

TABLE 9A-continued

The Effect of Compounds of Formula I on Lipoxygenase Activity
(LTB$_4$ Production)

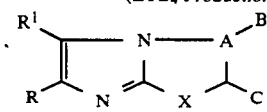

Formula (I)

| Compound Number | R$^1$ | R | A | X | n | 5-LO$^{(a)(b)}$ IC$_{50}$($\mu$M) |
|---|---|---|---|---|---|---|
| 28 | 4-pyridyl | 4-fluorophenyl | CH$_2$ | S(O)n | 1 | 1000 |
| 29 | 4-pyridyl | 4-fluorophenyl | CH$_2$ | S(O)n | 2 | >100 |
| 30 | 4-fluorophenyl | 4-fluorophenyl | CH$_2$ | S(O)n | 1 | 60 |
| 31 | 4-fluorophenyl | 4-fluorophenyl | CH$_2$ | S(O)n | 2 | <33 |
| 32 | 4-methylthiophenyl | 4-methylthiophenyl | CH$_2$ | S(O)n | 0 | >100 |
| 33 | phenyl | phenyl | CH$_2$ | S(O)n | 0 | NT |
| 34 | 4-methylphenyl | 4-methylphenyl | CH$_2$ | S(O)n | 0 | NT |
| 35 | 4-(prop-2-ene-oxy)phenyl | 4-(prop-2-ene-oxy)phenyl | CH$_2$ | S(O)n | 0 | NT |
| 36 | 4-(2,2,2-trifluoroethoxy)phenyl | 4-(2,2,2-trifluoroethoxy)phenyl | CH$_2$ | S(O)n | 0 | NT |
| 37 | 3,4,5-trimethoxyphenyl | 3,4,5-trimethoxyphenyl | CH$_2$ | S(O)n | 0 | NT |
| 38 | 4-pyridyl | 4-acetamidophenyl | CH$_2$ | S(O)n | 0 | 30 |

$^{(a)}$IC$_{50}$ determined on LTB$_4$ production by RBL$^{-1}$ high speed supernatant.
$^{(b)}$Not tested

TABLE 10

The Effect of Compound 1, Indomethacin, Ibuprofen, Naproxen and Phenidone on the Production of PGE$_2$ by Mouse Peritoneal Exudate Cells

| Compound | IC$_{50}$ ($\mu$M) |
|---|---|
| Compound 1 | 0.7 |
| Indomethacin | 0.04 |
| Ibuprofen | 0.5 |
| Naproxen | 1.8 |
| Phenidone | 28.0 |

$^a$Release of PGE$_2$ was measured by RIA of cell free supernatants from LPS-stimulated, C. parvum-elicited peritoneal exudate cells as described in the Methods.

TABLE 11

The Effect of Compound 1 on the Production of LTB$_4$ by Peritoneal Exudate Cells from Animals Treated with Anti-Inflammatory Agents

| Treatment | % Inhibition of LTB$_4$ Synthesis$^a$ Experiment: | | |
|---|---|---|---|
| | 1 | 2 | 3 |
| Compound 1 (100 mg/kg/p.o.) | 90 | 23 | 100 |
| Phenidone (200 mg/kg/p.o.) | | 21 | 33 |
| Naproxen (50 mg/kg/p.o.) | 0 | 15 | 0 |

$^a$Peritoneal exudate cells, harvested from control and drug-treated mice, were incubated in vitro with the calcium ionophore A23187 to stimulate LTB$_4$ production as described in the Methods. The results are expressed as the percentage inhibition of LTB$_4$ production in cells from drug-treated animals versus untreated control animals. Measurements were made on ten animals in each group for each experiment. Cells not exposed to A23187 did not release detectable LTB$_4$.

TABLE 12

Effect of Compound 1 on Hindleg Paralysis in Experimental Allergic Encephalomyelitis Induced in Lewis Female Rats

| COMPOUND (DOSE)* | HINDLEG PARALYSIS - CUMULATIVE INCIDENCE | |
|---|---|---|
| | DAY 9 TO 13 | DAY 14 TO 18 |
| Compound 1 (60) | 10/12 | 0/11** |
| INDOMETHACIN (2) | 6/11 | 10/11 |
| METHOTREXATE (0.3) | 0/11** | 0/11** |
| CONTROL | 12/16 | 14/16 |

*Mg/kg/day, p.o. days 0-4, 7-11, 14-18.
**Significantly different from control (p < 0.01).

TABLE 13

Effect of Compounds of Formula (I) in Inhibiting LTC$_4$ Production

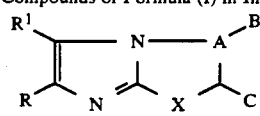

Formula I

| Compound Number | R$^1$ | R | A | X | n | IC$_{50}$$^{(a)(b)}$ ($\mu$M) |
|---|---|---|---|---|---|---|
| 1 | 4-pyridyl | 4-fluorophenyl | CH$_2$ | S(O)n | 0 | 1.8$^{(c)}$ |
| 2 | 4-pyridyl | 4-(1-propyl)aminophenyl | CH$_2$ | S(O)n | 0 | NT |
| 3 | 4-(pyrrolidin-1-yl)phenyl | 4-(pyrrolidin-1-yl)phenyl | CH$_2$ | S(O)n | 0 | NT |
| 4 | 4-(piperidin-1-yl)phenyl | 4-(piperidin-1-yl)phenyl | CH$_2$ | S(O)n | 0 | NT |
| 5 | 4-pyridyl | 3,4-(methylenedioxy)phenyl | CH$_2$ | S(O)n | 0 | NT |
| 6 | 4-fluorophenyl | 4-dimethylaminophenyl | CH$_2$ | S(O)n | 0 | NT |

TABLE 13-continued
Effect of Compounds of Formula (I) in Inhibiting LTC$_4$ Production Formula I $$R^1\underset{R\phantom{xx}N}{\overset{\phantom{x}}{\diagdown}}\underset{\phantom{xx}}{\overset{\phantom{x}}{\diagup}}N\!-\!-\!-\!A\!\diagdown\!\!^B_C$$
(with X between the ring atoms)

| Compound Number | R$^1$ | R | A | X | n | IC$_{50}$$^{(a)(b)}$ ($\mu$M) |
|---|---|---|---|---|---|---|
| 7 | 3,4-(methylenedioxy)phenyl | 4-pyridyl | CH$_2$ | S(O)n | 0 | NT |
| 8 | 4-fluorophenyl | 4-fluorophenyl | CH$_2$ | CH$_2$ | 0 | NT |
| 9 | 4-dimethylaminophenyl | 4-diethylaminophenyl | CH$_2$ | S(O)n | 0 | NT |
| 10 | 4-dimethylaminophenyl | 4-fluorophenyl | CH$_2$ | S(O)n | 0 | NT |
| 11 | 4-pyridyl | 4-pyridyl | CH$_2$ | S(O)n | 0 | NT |
| 12 | 4-fluorophenyl | 4-pyridyl | CH$_2$ | S(O)n | 0 | NS |
| 13 | 4-cyanophenyl | 4-cyanophenyl | CH$_2$ | S(O)n | 0 | NT |
| 14 | 4-fluorophenyl | 4-methoxyphenyl | CH$_2$ | S(O)n | 0 | NT |
| 15 | 4-trifluoromethylphenyl | 4-trifluoromethylphenyl | CH$_2$ | S(O)n | 0 | NT |
| 16 | 3,4-methylenedioxyphenyl | 3,4-methylenedioxyphenyl | CH$_2$ | S(O)n | 0 | NT |
| 17 | 4-ethylaminophenyl | 4-ethylaminophenyl | CH$_2$ | S(O)n | 0 | 1.2 |
| 18 | 4-pyridyl | 4-methoxyphenyl | CH$_2$ | S(O)n | 0 | 9.9 |
| 19 | 4-fluorophenyl | 4-fluorophenyl | CH$_2$ | S(O)n | 0 | NT |
| 20 | 4-methoxyphenyl- | 4-methoxyphenyl | CH$_2$ | S(O)n | 0 | NT |
| 21 | 4-methoxyphenyl | 4-methoxyphenyl | CH$_2$ | S(O)n | 0 | NT |
| 22 | 4-methoxyphenyl | 4-methoxyphenyl | CH$_2$ | CH$_2$ | 0 | NT |
| 23 | 4-pyridyl | 4-(pyrrolidin-1-yl)phenyl | CH$_2$ | S(O)n | 0 | NT |
| 24 | 4-fluorophenyl | 4-fluorophenyl(hydrate) | CH$_2$ | S(O)n | 0 | NT |
| 25 | 4-trifluoromethylphenyl | 4-trifluoromethylphenyl (hydrate) | CH$_2$ | S(O)n | 0 | NT |
| 26 | 2-pyridyl | 4-fluorophenyl | CH$_2$ | S(O)n | 0 | NT |
| 27 | 4-fluorophenyl | 2-pyridyl | CH$_2$ | S(O)n | 0 | NT |
| 28 | 4-pyridyl | 4-fluorophenyl | CH$_2$ | S(O)n | 1 | 0.5 |
| 29 | 4-pyridyl | 4-fluorophenyl | CH$_2$ | S(O)n | 2 | 0.5 |
| 30 | 4-fluorophenyl | 4-fluorophenyl | CH$_2$ | S(O)n | 1 | NT |
| 31 | 4-fluorophenyl | 4-fluorophenyl | CH$_2$ | S(O)n | 2 | NT |
| 32 | 4-methylthiophenyl | 4-methylthiophenyl | CH$_2$ | S(O)n | 0 | NT |
| 33 | phenyl | phenyl | CH$_2$ | S(O)n | 0 | NT |
| 34 | 4-methylphenyl | 4-methylphenyl | CH$_2$ | S(O)n | 0 | NT |
| 35 | 4-(prop-2-ene-oxy)phenyl | 4-(prop-2-ene-oxy)phenyl | CH$_2$ | S(O)n | 0 | NT |
| 36 | 4-(2,2,2-trifluoroethoxy)phenyl | 4-(2,2,2-trifluoroethoxy)phenyl | CH$_2$ | S(O)n | 0 | NT |
| 37 | 3,4,5-trimethoxyphenyl | 3,4,5-trimethoxyphenyl | CH$_2$ | S(O)n | 0 | NT |
| 38 | 4-pyridyl | 4-acetamedophenyl | CH$_2$ | S(O)n | 0 | NT |

$^{(a)}$NT = not tested; NS = not significant
$^{(b)}$IC$_{50}$ determined on LTB$_4$ production by human monocytes
$^{(c)}$average value based on 4 separate tests

COMPOSITION EXAMPLES

Example A

Capsule Composition

A pharmaceutical composition of this invention in the form of a capsule is prepared by filling a standard two-piece hard gelatin capsule with 50 mg of a compound of Formula (IC), in powdered form, 110 mg of lactose, 32 mg of talc and 8 mg of magnesium stearate.

Example B

Injectable Parenteral Composition

A pharmaceutical composition of this invention in a form suitable for administration by injection is prepared by stirring 1.5% by weight of a compound of Formula (IC) in 10% by volume propylene glycol and water. The solution is sterilized by filtration.

Example C

Ointment Composition

Compound of Formula (IC) 1.0 g
White soft paraffin to 100.0 g

The compound of Formula (IC) is dispersed in a small volume of the vehicle and gradually incorporated into the bulk of the vehicle to produce a smooth, homogeneous product. Collapsible metal tubes are then filled with the dispersion.

Example D

Topical Cream Composition

Compound of Formula (IC) 1.0 g
Polawax GP 200 20.0 g
Lanolin Anhydrous 2.0 g
White Beeswax 2.5 g
Methyl hydroxybenzoate 0.1 g
Distilled Water to 100.0 g The polawax, beeswax and lanolin are heated together at 60° C. A solution of methyl hydroxybenzoate is added and homogenization is achieved using high speed stirring. The temperature is then allowed to fall to 50° C. The compound of Formula (IC) is then added and dispersed throughout, and the composition is allowed to cool with slow speed stirring.

Example E

Topical Lotion Composition

Compound of Formula (IC) 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g Purified Water B.P. to 100.00 ml The methyl hydroxybenzoate and glycerin are dissolved in 70 ml of the water at 75°. The sorbitan monolaurate, polysorbate 20 and cetostearyl alcohol are melted together at 75° C. and added to the aqueous solution. The resulting emulsion is homogenized, allowed to cool with continuous stirring and the compound of Formula (IC) is added as a suspension in the remaining water. The whole suspension is stirred until homogenized.

Example F

Eye Drop Composition

Compound of Formula (IC) 0.5 g
Methyl Hydroxybenzoate 0.01 g
Propyl Hydroxybenzoate 0.04 g
Purified Water B.P. to 100.00 ml The methyl and propyl hydroxybenzoates are dissolved in 70 ml purified water at 75° C. and the resulting solution is allowed to cool. The compound of Formula (IC) is then added, and the solution is made up to 100 ml with purified water. The solution is sterilized by filtration through a membrane filter (0.22 mu m pore size) and packed aseptically into suitable sterile containers.

Example G

Composition for Administration by Inhalation

For an aerosol container with a capacity of 15-20 ml: Mix 10 mg of a compound of Formula (IC) with 0.1-0.2% of a lubricating agent, such as Span 85 or oleic acid, and disperse such mixture in a propellant (c.a.), such as freon, preferably in a combination of freon 114 and freon 12, and put into an appropriate aerosol container adapted for either intranasal or oral inhalation administration.

Example H

Composition for Administration by Inhalation

For an aerosol container with a capacity of 15-20 ml: Dissolve 10 mg of a compound of Formula (IC) in ethanol (6-8 ml), add 0.1-0.2% of a lubricating agent, such as Span 85 or oleic acid; and disperse such in a propellant (c.a.), such as freon, preferably a combination of freon 114 and freon 12, and put into an appropriate aerosol container adapted for either intranasal or oral inhalation administration.

What is claimed is:

1. A method of treating a 5-lipoxygenase pathway mediated disease, other than a 5-lipoxygenase pathway mediated disease which is also mediated by the cyclooxygenase enzyme, in an animal which comprises administering an effective amount of a compound of the formula:

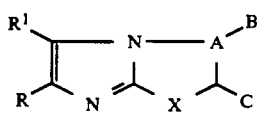

Formula (I)

wherein
X is $S(O)_n$;
n is 0, 1 or 2;
A is $CH_2$;
B and C are independently selected from H, methyl, ethyl or dimethyl;
$R^1$ and R are independently selected from (a) pyridyl;
(b) phenyl;
(c) monosubstituted phenyl wherein said substituent is selected from $C_{1-3}$ alkoxy, halo, $CF_3$, $C_{1-3}$ alkylthio, $C_{1-4}$ alkyl, 2,2,2-trihaloethoxy, prop-2-ene-1-oxy, $C_{1-3}$ alkylamino, $C_{1-3}$ dialkylamino, cyano, pyrrolidino or piperidino;
(d) disubstituted phenyl wherein said substituents are independently selected from $C_{1-4}$ alkyl or $C_{1-3}$ alkoxy or the disubstituents together form a methylenedioxy group;
(e) 3,4,5-trimethoxyphenyl;

or a pharmaceutically acceptable salt thereof provided that:

(1) when either of R or $R^1$ is cyanophenyl the other must be cyanophenyl or 4-pyridyl;
(2) when R or $R^1$ is phenyl substituted in the 2,3,5, or 6 position with $C_{1-3}$ alkylamino; $C_{1-3}$ dialkylamino, pyrrolidino, or piperidino, the other of R or $R^1$ must be 4-pyridyl.

2. The method of claim 1 wherein $R^1$ and R are both 4-(pyrrolidin-1-yl)phenyl, X is $S(O)n$, A is $CH_2$ and n is 0.

3. The method of claim 1 wherein R is 4-fluorophenyl, $R^2$ is 4-dimethylaminophenyl, X is $S(O)n$, A is $CH_2$ and n is 0.

4. The method of claim 1 wherein $R^1$ and R are both 4-diethylaminophenyl, X is $S(O)n$, A is $CH_2$ and n is 0.

5. The method of claim 1 wherein $R^1$ is 4-fluorophenyl, R is 4-methoxyphenyl, X is $S(O)n$, A is $CH_2$ and n is 0.

6. The method of claim 1 wherein $R^1$ is 4-pyridyl, R is 4-(pyrrolidin-1-yl)phenyl, 4-acetamidophenyl or 4-(N-propylacetamido)phenyl, X is $S(O)n$, A is $CH_2$ and n is 0.

7. The method of claim 1 wherein $R^1$ is 4-pyridyl, R is 4-fluorophenyl, X is $S(O)n$, A is $CH_2$ and n is 0.

8. The method of claim 1 wherein $R^1$ is 4-pyridyl, R is 4-fluorophenyl, X is $S(O)n$, A is $CH_2$ and n is 1.

9. The method of claim 1 wherein $R^1$ is 4-pyridyl, R is 4-fluorophenyl, X is $S(O)n$, A is $CH_2$ and n is 2.

10. The method of claim 1 wherein $R^1$ is 4-pyridyl, R is 4-(1-propylamino)phenyl, A is $CH_2$, X is $S(O)n$ and n is 0.

11. The method of claim 1 wherein $R^1$ and R are both 4-(piperidin-1-yl)phenyl, A is $CH_2$, X is $S(O)n$ and n is 0.

12. The method of claim 1 wherein $R^1$ is 3, 4-(methylenedioxy)phenyl, R is 4-pyridyl, A is $CH_2$, X is $S(O)n$ and n is 0.

13. The method of claim 1 wherein R and $R^1$ are 4-fluorophenyl, A is $CH_2$ and X is $CH_2$.

14. The method of claim 1 wherein $R^1$ and R are both 4-trifluoromethylphenyl, A is $CH_2$, and X is $S(O)n$ and n is 0.

15. The method of claim 1 wherein $R^1$ and R are both 3,4-methylenedioxyphenyl, A is $CH_2$, X is $S(O)n$ and n is 0.

16. The method of claim 1 wherein $R^1$ and R are both 4-ethylaminophenyl, A is $CH_2$, X is $S(O)n$ and n is 0.

17. The method of claim 1 wherein $R^1$ is 4-pyridyl, R is 4-methoxyphenyl, A is $CH_2$, X is $S(O)n$ and n is 0.

18. The method of claim 1 wherein $R^1$ and R are both 4-fluorophenyl, A is $CH_2$ and X is $S(O)n$ and n is 0.

19. The method of claim 1 wherein R and $R^1$ are both 4-methoxyphenyl, A is $CH_2CH_2$, X is $S(O)n$ and n is 0.

20. The method of claim 1 wherein R and $R^1$ are both 4-methoxyphenyl, A is $CH_2$, X is $S(O)n$ and n is 0.

21. The method of claim 1 wherein R and R¹ are both 4-methoxyphenyl, A is CH₂, and X is CH₂.

22. The method of claim 1 wherein R and R¹ are both 4-pyridyl, A is CH₂, X is S(O)n and n is 0.

23. The method of claim 1 wherein the administration is oral.

24. The method of claim 1 wherein the administration is parenteral.

25. The method of claim 1 wherein the administration is topical.

26. The method of claim 1 wherein the adminstration is by inhalation.

27. A method of inhibiting the 5-lipoxygenase enzyme in an animal which comprises administering to such animal an effective 5-lipoxygenase inhibiting amount of a compound of the formula

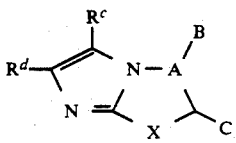

Formula (IC)

wherein
X is S(O)n;
n is 0, 1, or 2;
A is CH₂;
B and C are independently selected from H, methyl, ethyl or gem-dimethyl;
one of $R^c$ or $R^d$ must be selected from
 a) 2-pyridyl, 3-pyridyl, or 4-pyridyl;
 b) monosubstituted phenyl wherein said substituent is selected from $C_{1-3}$ dialkylamino, $C_{1-3}$ alkylamino, pyrrolidino, piperidino, cyano, 2,2,2-trihaloethoxy, alkanamido, N-($C_{1-3}$ alkyl)-($C_{1-3}$ alkanamido) or prop-2-ene-1-oxy; or
 c) disubstituted phenyl wherein said substituents are independently selected from $C_{1-4}$ alkyl or $C_{1-3}$ alkoxy or the di-substituents together form a methylenedioxy group; and
the other of $R^c$ or $R^d$ is selected from:
 1) pyridyl;
 2) phenyl;
 3) monosubstituted phenyl wherein said substituent is selected from $C_{1-3}$ alkoxy, halo, CF₃, $C_{1-3}$ alkylthio, $C_{1-4}$ alkyl, 2,2,2-trihaloethoxy, prop-2-ene-1-oxy, $C_{1-3}$ alkylamino, $C_{1-3}$ dialkylamino, cyano, pyrrolidino, or piperidino;
 4) disubstituted phenyl wherein said substituents are independently selected from $C_{1-4}$ alkyl or $C_{1-3}$ alkoxy, or the disubstituents together form a methylenedioxy group; or
 5) 3, 4, 5-trimethoxyphenyl;
provided that:
(a) when X is (SO)n and n is 0, both or $R^c$ and $R^d$ are not simultaneously 2-, 3-, or 4-pyridyl; when n is 1, and one of $R^c$ or $R^d$ is 2-pyridyl or 3-pyridyl the other of $R^c$ or $R^d$ is not 2-pyridyl or 3-pyridyl; when n is 2, and one of $R^c$ and $R^d$ is 2-pyridyl the other of $R^c$ and $R^d$ is not 2-pyridyl; and when n is 0 and one of $R^c$ and $R^d$ is phenyl the other of $R^c$ and $R^d$ is not 2-, 3-, or 4-pyridyl;

(b) when X is (SO)n and n is 0, both of $R^c$ and $R^d$ are other than phenyl substituted in the 2, 3, 5, or 6-position with $C_{1-3}$ alkylamino, $C_{1-3}$ dialkylamino, or pyrrolidino, or piperidino;

(c) only one of $R^c$ or $R^d$ is $C_{1-3}$alkylaminophenyl;

(d) only of $R^c$ or $R^d$ is $C_{1-3}$ dialkylamino;

(e) when either of $R^c$ or $R^d$ is disubstituted phenyl the other must be 4-pyridyl;

(f) when either of $R^c$ or $R^d$ is cyanophenyl the other must be cyanophenyl or 4-pyridyl;

(g) when either of $R^c$ or $R^d$ is phenyl substituted in the 2, 3, 5, or 6-position with $C_{1-3}$alkylamino, $C_{1-3}$ dialkylamino, pyrrolidino or piperidino, the other must be 4-pyridyl;

(h) only of $R^c$ or $R^d$ is (4-prop-2-ene-1-oxy)phenyl;

(i) only of $R^c$ or $R^d$ is 4-(2,2,2-trifluoroethoxy) phenyl;

only of $R^c$ or $R^d$ is 3,4-methylenedioxy phenyl;

(k) when X is S(O)n, and n is 0, and one of $R^c$ or $R^d$ is 4-pyridyl, the other is not 4-pyridyl, phenyl, 4-methoxyphenyl, 4-fluorophenyl, 4-methylthiophenyl, 2-bromophenyl, 3-chlorophenyl, 4-trifluoromethylphenyl, 4-methylphenyl, 4-ethylphenyl, 3-isopropoxyphenyl, 4-methoxyphenyl or 4-ethoxyphenyl;

(l) when $R^d$ is N-($C_{1-3}$ alkanamido) or N-($C_{1-3}$ alkyl)-($C_{1-3}$alkanamido), $R^c$ must by 4-pyridyl;

(m) when X is S(O)n, and n is 1, and one of $R^c$ or $R^d$ is 4-pyridyl, the other is not 4-pyridyl, phenyl, or phenyl mono-substituted by 4-methoxy, 4-ethoxy, or 4-fluoro;

(n) when X is S(O)n, and n is 0, 1 or 2, and one of $R^a$ or $R^b$ is phenyl, the other is not a phenyl di-substituted with methoxy;

or a pharmaceutically acceptable salt thereof.

28. The method of claim 27 wherein $R^c$ is 4-pyridyl, $R^d$ is 4-(1-propyl)aminophenyl, A is CH₂, X is S(O)ₙ and n is 0.

29. The method of claim 27 wherein $R^c$ is 4-pyridyl, $R^d$ is 4-(pyrrolidin-1-yl)phenyl, A is CH₂, X is S(O)ₙ and n is 0.

30. The method of claim 27 wherein $R^c$ and $R^d$ are both 4-(pyrrolidin-1-yl)phenyl, A is CH₂, X is S(O)ₙ and n is 0.

31. The method of claim 27 wherein $R^c$ and $R^d$ are both 4-(piperidino-1-yl)phenyl, A is CH₂, X is S(O)ₙ and n is 0.

32. The method of claim 27 wherein $R^c$ is 4-fluorophenyl, $R^d$ is 4-dimethylaminophenyl, A is CH₂, X is S(O)ₙ and n is 0.

33. The method of claim 27 wherein $R^c$ is 3,4-methylenedioxyphenyl, $R^d$ is 4-pyridyl, A is CH₂, X is S(O)ₙ and n is 0.

34. The method of claim 27 wherein $R^c$ is 3,4-methylenedioxyphenyl, $R^d$ is 4-fluorophenyl, A is CH₂, X is S(O)ₙ and n is 0.

35. The method of claim 27 wherein $R^c$ and $R^d$ are both 4-cyanophenyl, A is CH₂, X is S(O)ₙ and n is 0.

36. The method of claim 27 wherein $R^c$ is 4-pyridyl, $R^d$ is 4-(pyrrolidin-1-yl)phenyl, 4-(acetamido)phenyl or 4-(N-propylacetamido)phenyl, A is CH₂, X is S(O)ₙ and n is 0.

37. The method of claim 27 wherein $R^c$ is 2-pyridyl, $R^d$ is 4-(pyrrolidin-1-yl)phenyl, A is CH₂, X is S(O)ₙ and n is 0.

38. The method of claim 27 wherein $R^c$ is 4-fluorophenyl, $R^d$ is 2-pyridyl, A is CH₂, X is S(O)ₙ and n is 0.

39. The method of claim 27 wherein $R^c$ and $R^d$ are 4-pyridyl, A is CH₂, X is S(O)ₙ and n is 0.

40. The method of claim 27 wherein the administration is selected from oral, topical, parenteral or inhalation means.

41. A method of inhibiting the 5-lipoxygenase enzyme in an animal which comprises administering to such animal an effective 5-lipoxygenase inhibiting amount of 5-(4-pyridyl)-6-(4-fluorophenyl)-2,3-dihydroimidazo[2,1-b]thiazole-S-dioxide.

42. The method of claim 1 wherein both of $R^1$ and R are 4-fluorophenyl, X is $S(O)_n$, n is 2 and A is $CH_2$.

* * * * *